United States Patent [19]
Nagy et al.

[11] Patent Number: 5,985,852
[45] Date of Patent: Nov. 16, 1999

[54] INHIBITION OF SELECTIN BINDING

[75] Inventors: Jon O. Nagy, Rodeo; Wayne R. Spevak, Albany, both of Calif.; Falguni Dasgupta, New Delhi, India; Caroline Bertozzi, Albany, Calif.

[73] Assignee: The Regents of the University of California

[21] Appl. No.: 09/250,999

[22] Filed: Feb. 16, 1999

Related U.S. Application Data

[62] Division of application No. 08/807,428, Feb. 28, 1997
[60] Provisional application No. 60/012,894, Mar. 1, 1996.

[51] Int. Cl.$^6$ .................. A61K 31/715; A61K 9/127; C07H 1/00
[52] U.S. Cl. ...................... 514/54; 514/23; 514/25; 514/53; 514/61; 514/62; 536/1.11; 536/4.1; 536/17.2; 536/18.7; 536/53; 536/55; 536/55.1; 536/55.2; 424/450
[58] Field of Search .......................... 514/23, 25, 53, 514/54, 61, 62; 424/450; 536/1.11, 4.1, 17.2, 18.7, 53, 55, 55.1, 55.2

[56] References Cited

U.S. PATENT DOCUMENTS

| | | | |
|---|---|---|---|
| 5,464,935 | 11/1995 | Heavner et al. | 530/329 |
| 5,470,843 | 11/1995 | Stahl et al. | 514/61 |
| 5,486,536 | 1/1996 | Ward et al. | 514/460 |
| 5,489,578 | 2/1996 | Rosen et al. | 514/61 |
| 5,512,294 | 4/1996 | Li et al. | 424/450 |
| 5,576,305 | 11/1996 | Ratcliffe | 514/25 |

FOREIGN PATENT DOCUMENTS

| | | |
|---|---|---|
| WO 91/19501 | 12/1991 | WIPO. |
| WO 92/07572 | 5/1992 | WIPO. |
| WO 96/34609 | 11/1996 | WIPO. |

OTHER PUBLICATIONS

Alon et al., "Lifetime of the P–selectin–carbohydrate bond and its response to tensile force in hydrodynamic flow" *Nature* (1995) 374:539–542.
Arbones et al., "Lymphocyte homing and leukocyte rolling and migration are impaired in L–selectin–deficient mice" *Immunity* (1994) 1:247–260.
Aruffo et al., "CD62/P–selectin recognition of myeloid and tumor cell sulfates" *Cell* (1991) 67:35–44.
Aruffo et al., "Molecular cloning of a CD28 cDNA by high–efficiency COS cell expression system" *Proc. Natl. Acad. Sci. USA* (1987) 84:8573–8577.
Aruffo et al., "Granule membrane protein 140 (GMP140) binds to carcinomas and carcinoma–derived cell lines" *Proc. Natl. Acad. Sci. USA* (1992) 89:2292–2296.
Bertozzi et al., "Sulfated disaccharide inhibitors of L–selectin: Deriving structural leads from a physiological selectin ligand" *Biochemistry* (1995) 34(44):14271–14278.
Brandley et al., "Structure—function studies on selectin carbohydrate ligands. Modifications to fucose, sialic acid and sulphate as a sialic acid replacement" *Glycobiol.* (1993) 3(6):633–641.

Cecconi et al., "Inositol Polyanions" *J. Biol. Chem.* (1994) 269:15060–15066.
Charych et al., "A 'litmus test' for molecular recognition using artificial membranes" *Chem. Biol.* (1996) 3:113–120.
Charych et al., "Direct colorimetric detection of a receptor–ligand interaction by a polymerized bilayer assembly" *Science* (1993) 261:585–588.
DeFrees et al., "Ligand recognition by E–selectin: Synthesis, inhibitory activity, and conformational analysis of bivalent sialyl lewis x analogs" *J. Am. Chem. Soc.* (1995)117:66–79.
DeFrees et al., "Sialyl lewis x liposomes as a multivalent ligand and inhibitor of E–selectin mediated cellular adhesion" *J. Am. Chem. Soc.* (1996) 118(26):6101–6104.
Dupre et al., "Glycomimetic selection inhibitors: (α–D–Mannopyranosyloxy) Methylbiphenyls" *Bioorg. Med. Chem. Lett.* (1996) 6:569–572.
Foxall et al., "The three members of the selectin receptor family recognize a common carbohydrate epitope, the sialyl lewis$^x$ oligosaccharide" *J. Cell. Biol.* (1992) 117(4):895–902.
Frankel et al., "Supramolecular assemblies of diacetylenic aldonamides" *J. Am. Chem. Soc.* (1991) 113:7436–7437.
Fuhrhop et al., "Supramolecular assemblies, a crystal structure, and a polymer of N–diacetylenic gluconamides" *J. Am. Chem. Soc.* (1991) 113:7437–7439.
Geng et al., "Rapid neutrophil adhesion to activated endothelium mediated by GMP–140" *Nature* (1990) 343:757–760.
Hanessian et al., "Design and synthesis of glycomimetic prototypes—a model sialyl lewis$^x$ ligand for E–selectin" *J. Syn. Lett.* (1994) 868–870.
Hindsgaul, "Synthesis of carbohydrates for applications in glycobiology" *Sem. Chem. Biol.* (1991) 2:319–326.
Hiruma et al., "Rational design and synthesis of a 1, 1–linked disaccharide that is 5 times as active as sialyl lewis x in binding to E–selectin" *J. Am. Chem. Soc.* (1996) 118:9265–9270.
Hosomi et al., "Highly stereoselective C–allylation of glycopyranosides with allylsilanes catalyzed by silyl triflate or iodosilane" *Tetrahedron Lett.* (1984) 25:2383–2386.
Hub et al., "Polymerizable phospholipid analogues—New stable biomembrane and cell models" *Angew. Chem. Int. Ed. Engl.* (1980) 19(11):938–940.

(List continued on next page.)

*Primary Examiner*—Kathleen K. Fonda
*Attorney, Agent, or Firm*—David J. Aston; Pepi Ross; John W. Mahoney

[57] ABSTRACT

This invention provides compositions for inhibiting the binding between two cells, one expressing P- or L-selectin on the surface and the other expressing the corresponding ligand. A covalently crosslinked lipid composition is prepared having saccharides and acidic group on separate lipids. The composition is then interposed between the cells so as to inhibit binding. Inhibition can be achieved at an effective oligosaccharide concentration as low as $10^6$ fold below that of the free saccharide. Since selectins are involved in recruiting cells to sites of injury, these composition scan be used to palliate certain inflammatory and immunological conditions.

20 Claims, 8 Drawing Sheets

OTHER PUBLICATIONS

Hupfer et al., "Liposomes from polymerizable phospholipids " *Chem. Phys. Lipids* (1983) 33:355–374.

Ichikawa et al., "Enzyme–catalyzed oligosaccharide synthesis" *Anal. Biochem.* (1992) 202:215–238.

Imai et al., "Sulphation requirement for GlyCam–1, an endothelial ligand for L–selectin" *Nature* (1993) 361:555–557.

Ito et al., "Synthesis of bioactive sialosides" *Pure Appl. Chem.* (1993) 65(4):753–762.

Kansas, "Selectins and their ligands: Current concepts and controversies" *Blood* (1996) 88(9):3259–3287.

Kunitake et al., "Synthetic bilayer membranes with anionic head groups" *Bull. Chem. Soc. Japan* (1978) 51(6):1877–1879.

Lasky, "Selectin–carbohydrate interactions and the initiation of the inflammatory response" *Annu. Rev. Biochem.* (1995) 64:113–139.

Ley et al., "Shear–dependent inhibition of granulocyte adhesion to cultured endothelium by dextran sulfate" *Blood* (1989) 73(5):1324–1330.

Lin et al., "Liposome–like fucopeptides as sialyl lewis x mimetics" *Bioorg. Med. Chem. Lett.* (1996) 6(22):2755–2760.

Lockhoff et al., "Glycolipids as immunomodulators: Syntheses and properties" *Angew. Chem. Int. Ed. Engl.* (1991) 30:1161–1620.

Martens et al., "Peptides which bind to E–selectin and block neutrophil adhesion" *J. Biol. Chem.* (1995) 270(36):21129–21136.

McEver et al., "Leukocyte trafficking mediated by selectin––carbohydrate interactions" *J. Bio. Chem.* (1995) 270(19):11025–11028.

Moore et al., "GMP–140 binds to a glycoprotein receptor on human neutrophils: Evidence for a Lectin–like interaction" *J. Cell Biol.* (1991) 112(3):491–499.

Moore et al., "P–Selectin glycoprotein ligand–1 mediates rolling of human neutrophils on P–Selectin" *J. Cell Biol.* (1995) 128(4):661–671.

Mullane et al., "Myeloperoxidase activity as a quantitative assessment of neutrophil infiltration into ischemic myocardium" *J. Pharmacol. Meth.* (1985) 14:157–167.

Murohara et al., "Cardioprotection by liposome–conjugated sialyl Lewis$^x$–oligosaccharide in myocardial ischaemia and reperfusion injury" *Cardiovasc. Res.* (1995) 30:965–974.

Nagy et al., "The chemical–enzymatic synthesis of a carbon glycoside of N–acetyl neuraminic acid" *Tetrahedron Lett.* (1991) 32(32):3953–3956.

Needham et al., "The HNK–1 reactive sulfoglucuronyl glycolipids are ligands for L–selectin and P–selectin but not E–selectin" *Proc. Natl. Acad. Sci. USA* (1993) 90:1359–1363.

Nelson et al., "Heparin oligosaccharides bind L– and P–Selectin and inhibit acute inflammation" *Blood* (1993) 82(11):3253–3258.

Nelson et al., "Higher–affinity oligosaccharide ligands for E–selectin" *J. Clin. Invest.* (1993) 91:1157–1166.

Norgard–Sumnicht et al., "Calcium–dependent heparin–like ligands for L–Selectin in nonlymphoid endothelial cells" *Science* (1993) 261:480–483.

Palabrica et al., "Leukocyte accumulation promoting fibrin deposition is mediated in vivo by P–selectin on adherent platelets" *Nature* (1992) 359:848–851.

Phillips et al., "ELAM–1 mediates cell adhesion by recognition of a carbohydrate ligand, sialyl–le$^x$" *Science* (1990) 250:1130–1132.

Pouyani et al., "PSGL–1 recognition of P–selectin is controlled by a tyrosine consensus at the PSGL–1 amino terminus" *Cell* (1995) 83:333–343.

Reichert et al., "Polydiacetylene liposomes functionalized with sialic acid bind and colorimetrically detect influenza virus" *J. Am. Chem. Soc.* (1995) 117:829–830.

Ringsdorf et al., "Molecular architecture and function of polymeric oriented systems: models for the study of organization, surface recognition, and dynamics of biomembranes" *Angew. Chem. Int. Ed. Eng.* (1988) 27:113–158.

Roy et al., "Synthesis of antigenic carbohydrate polymers recognized by lectins and antibodies" *J. Chem. Soc. Chem. Comm.* (1988) 1058–1060.

Sako et al., "A sulfated peptide segment at the amino terminus of PSGL–1 is critical for P–selectin binding" *Cell* (1995) 83:323–331.

Sears et al., "Intervention of carbohydrate recognition by proteins and nucleic acids" *Proc. Natl. Acad. Sci. USA* (1996) 93:12086–12093.

Spevak, W.R., "The Presentation of Biological Ligands on the Surface of Polymerized Monolayers and Liposomes" Dissertation submitted in partial satisfaction of the requirements for the degree of Doctor of Philosophy in Chemistry, University of California at Berkeley, 1994, 198 pages total.

Dialog® Abstract of Spevak, W.R., "The Presentation of Biological Ligands on the Surface of Polymerized Monolayers and Liposomes" Dissertation submitted in partial satisfaction of the requirements for the degree of Doctor of Philosophy in Chemistry, University of California at Berkeley, 1994. One page total.

Spevak et al., "Polymerized liposomes containing C–glycosides of sialic acid: Potent inhibitors of influenza virus in vitro infectivity" *J. Amer. Chem. Soc.* (1993) 115:1146–1147.

Spevak et al., "An efficient synthesis of N–Allyglycosylamides from unprotected carbohydrates" *J. Org. Chem.* (1996) 61:3417–3422.

Spevak et al., "Carbohydrates in an acidic multivalent assembly: nanomolar P–Selectin inhibitors" *J. Med. Chem* (1996) 39:1018–1020.

Spevak et al., "Molecular assemblies of functionalized polydiacetylenes" *Advanced Materials* (1995) 7(1):85–89.

Stamper et al., "Lymphocyte homing into lymph nodes: In vitro demonstration of the selective affinity of recirculating lymphocytes for high–endothelial venules" *J. Exp. Med.* (1976) 144:828–833.

Stoolman et al., "Possible role for cell–surface carbohydrate–binding molecules n lymphocyte recirculation" *J. Cell. Biol.* (1988) 96:722–729.

Toone et al., "Enzyme–catalyzed synthesis of carbohydrates" *Tetrahedron* (1989) 45(17):5365–5422.

Wang et al., "Synthesis of phospholipid–inhibitor conjugates by enzymatic transphosphatidylation with phospholipase D" *J. Am. Chem. Soc.* (1993) 115:10487–10491.

Wang et al., "Synthesis of sialyl lewis x mimetics: Use of O–α–fucosyl–(1R, 2R)–2–aminocyclohexanol as core structure" *Tetrahedron Lett.* (1996) 37(31):5427–5430.

Warren et al., "Tumor necrosis factor participates in the pathogenesis of acute immune complex alveolitis in the rat" *J. Clin. Invest.* (1989) 84:1873–1882.

Watson et al., "The complement binding–like domains of the murine homing receptor facilitate lectin activity" *J. Cell Biol.* (1992) 115(1):235–243.

Wilkins et al., "Tyrosine sulfation of P–selectin glycoprotein ligand–1 is required for high affinity binding to P–selectin" *J. Biol. Chem.* (1995) 270:22677–22680.

(5%) sLe<sup>x</sup> analog (5%) sulfo Le<sup>x</sup> analog (5%) lactose analog (5%) maltose analog

| Selectin Ligand Fragments | Target Glycolipids |
|---|---|
| | ![structure] |
| Glucose | Glc β-1 lipid (1) |
| N Ac-Glucosamine | GlcNac β-1 lipid (2) |
| Galactose | Gal β-1 lipid (3) |
| Lactose | Lac β-1 lipid (4) |
| N Ac-Lactosamine | LacNAc β-1 lipid (5) |
| Fucose | Fuc β-1 lipid (6) |
| Fucose α-3-Glucose | Fuc α-3-Glc β-1 lipid (7) |
| Fucose α-4-Glucose | Fuc α-4-Glc β-1 lipid (8) |
| 3'-Sialyl lactose | NeuAc β-3'-Lac β-1 lipid (9) |

Sialyl fucosyl lactose 6,6'-disulfo-lactose sialyl Lewis X

"Tethered" analog ively as selectins. Each of these molecules is part of a ligand-
INHIBITION OF SELECTIN BINDING

CROSS-REFERENCE TO RELATED APPLICATIONS

This application is a division of pending U.S. patent application Ser. No. 08/807,428, filed Feb. 28, 1997, which claims priority benefit of U.S. provisional application No. 60/012,894, filed Mar. 1, 1996, both of which are hereby incorporated herein by reference in their entirety.

STATEMENT OF RIGHTS TO INVENTIONS MADE UNDER FEDERALLY SPONSORED RESEARCH

This invention was made in part during work partially supported by the U.S. Department of Energy under contract DE-AC03-76SF00098. The government has certain rights in the invention.

TECHNICAL FIELD

This invention relates generally to the field of therapeutic compounds designed to interfere between the binding of carbohydrate ligands and their receptors on cell surface. More specifically, it provides compositions of materials whose purpose is inhibiting cell migration and activation via P- and L-selectin, using polymerized glycoliposomes.

BACKGROUND

The adhesion of circulating neutrophils to endothelial cells is one of the important events occurring in the process of inflammation. Neutrophil recruitment to tissues is initiated by an adhesion cascade. Through this process, cells roll and eventually attach firmly to the endothelium. The factors that contribute to the high binding strength of this interaction are not fully understood, but is thought to involve interaction between selectins on one cell with carbohydrate ligands on another cell. By interfering with the binding between these components, it may be possible to counter pathological sequelae related to cell migration.

A number of adhesion molecules mediate the interaction of neutrophils and other leukocytes to the endothelium. Amongst them are the ICAMs, VCAM, CD11, CD18, the integrin I4v1, and several receptors now known collectively as selectins. Each of these molecules is part of a ligand-receptor pair, one of which is expressed on each of the two interacting cells. For a general review, the reader is referred to Bevilacqua (Annu. Rev. Immunol. 11:767, 1993). In various combinations, these and other molecules support leukocyte adhesion to the vessel wall and extravasation, and may also participate in activation of cell effector functions. Expression of many of these molecules is up-regulated by soluble factors such as cytokines, thereby acting to increase the recruitment of leukocytes to an affected area.

Amongst the plurality of adhesion molecules that have been described, three have been collected together in a category known as selectins. One was formerly known as ELAM-1, and was identified using inhibitory monoclonal antibodies against cytokine-activated endothelial cells. Another was formerly designated as PADGEM, GMP-140, or CD61. It was originally identified on platelets, and is now known as P-selectin. A third identified on lymphocytes was formerly designated as mLHR, Leu8, TQ-1, gp90$^{MEL}$, Lam-1, or Lecam-1, and is now known as L-selectin. The selectins were grouped together on the basis of a structural similarity, before very much was known about their binding specificity. All are single chain polypeptides having a carbohydrate binding domain near the N-terminus, an EGF repeat, and anywhere between 2 to 9 modules of ~60 amino acids each sharing homology with complement binding proteins. For general reviews, the reader is referred to Lasky (Annu. Rev. Biochem. 64:113, 1995) and Kansas (Blood 88:3259, 1996).

The three selectins differ from each other in a number of important respects. As depicted in FIG. 2A, the selectins have different ligand counterparts in the adhesion process. Each selectin is regulated differently, and participates in a different manner in the process of inflammation or immunity. There is also an increasing appreciation for differences in the ligand binding requirements between the selecting.

E-selectin has garnered a significant amount of recent research interest because of its role in inflammation. The migration of inflammatory mediator cells to an inflammatory site is thought to be mediated in part by adhesion of the cells to vascular endothelial cells. Studies in vitro have suggested that E-selectin participates in the adhesion of not only neutrophils, but also eosinophils, monocytes and a subpopulation of memory T-cells to endothelium that has been activated by endotoxin, IL-1, or TNF. Expression of E-selectin by endothelial monolayer increases by about 10-fold and peaks at about 4 hours after stimulation with IL-1, subsiding to near basal levels within 24 hours. The biological role of E-selectin is thought to be a strong binding of cells bearing a suitable E-selectin ligand, over a time-course of 20 min to 1 hour, particularly during the course of local inflammation.

Phillips et al. (Science 250:1130, 1990) first identified the binding target of E-selectin as the oligosaccharide sialyl Lewis X (sLe$^x$) (NeuAcI2,3Galv1,4(fucI1,3)GlcNac-), a terminal structure found on cell surface glycoprotein of neutrophils. This has become the prototype carbohydrate ligand for the selectin class. This and related oligosaccharides are the subject of U.S. Pat. No. 5,576,305 and PCT application WO 92/07572.

The sLe$^x$ unit has been assembled into various polymeric structures in an attempt to improve its weak binding to selectins. For example, U.S. Pat. No. 5,470,843 and DeFrees et al. (J. Am. Chem. Soc. 117:66, 1995) disclose bivalent sialyl X saccharides. U.S. Pat. No. 5,470,843 discloses a carbohydrate-containing polymer having a synthetic polymer backbone with 10–20 sLe$^x$, sLe$^a$, or GlcNac linked via a bifunctional spacer.

DeFrees et al. (J. Am. Chem. Soc. 118:6101, 1996) describe a sLe$^x$ preparation made with conventional phospholipid liposome technology. The liposomes contain phosphatidyl choline, cholesterol, phospholipid conjugated with methoxypolyethylene glycol, and phospholipid conjugated with sLe$^x$ through a polyethylene glycol spacer. Data is presented showing that this composition is 5×10$^3$ fold more potent than the sLe$^x$ monomer in inhibiting the binding of E-selectin to cells. Murohara et al. (Cardiovasc. Res. 30:965, 1995) tested sLe$^x$ phosphoboliposomes in a myocardial reperfusion model, and found that a dose of 400 Tg/kg body weight reduced the proportional size of the area of risk and necrosis.

P-selectin is a transmembrane glycoprotein of ~140 kDa, substantially larger than E-selectin. It was originally described on platelets, in which it may be found in I- and dense-granules. Upon activation of platelets with a mediator like thrombin, P-selectin is rapidly redistributed to the cell surface. In endothelial cells, it is found in granules known as Weibel-Palade bodies, from which it is redistributed to the surface upon activation with histamine. Shuttling of P-selectin to storage granules appears to be mediated by a sorting signal present in the cytoplasmic domain, and apparently unique in comparison with E-selectin.

Accordingly, P-selectin differs from E-selectin in that it may be rapidly expressed from storage granules rather than requiring de novo synthesis. P-selectin binds carbohydrate ligands present on neutrophils, monocytes, and memory T cells. Not only is P-selectin in a preformed state, its expression is stimulated by mediators such as histamine which in turn are preformed and stored in the granules of inflammatory cells. The adherence of leukocytes to P-selectin rather than E-selectin on endothelial cells is perhaps the initial event that occurs for recruitment of these cells to an injured site. Interference with P-selectin binding may be particularly important when it is desirable to limit leukocyte migration.

The presence of P-selectin on platelets suggests additional unique biological roles compared with the other selecting. In one hypothesis, sites of tissue injury may be acutely enriched with short-acting platelet activators, and active platelets expressing P-selectin may directly recruit other leukocytes. In another hypothesis, neutrophils or monocytes at an inflamed site may be able to catch platelets by way of the P-selectin, which in turn could lead to clot formation or additional mediator release. In an experimental thrombus model, it has been observed that platelets accumulate first at the injury site, followed by leukocyte adherence and fibrin deposition. Both of the latter two steps was inhibited by antibodies against P-selectin (Palabrica et al., Nature 359:848, 1992).

L-selectin has a number of features that are different from the other known selecting. First, the tissue distribution pattern is opposite to that of P- and E-selectin—it is expressed on the surface of leukocytes, rather than on the endothelium; while the ligand it binds to is on the endothelium rather than the leukocytes. Second, L-selectin is constitutively expressed, rather than being up-regulated during inflammation, and is in fact shed following activation. This may act to allow the activated cells to be released after binding, or may indicate a role of L-selectin in cellular activation. Third, L-selectin is present not only on neutrophils and monocytes, but also on most lymphocytes; while the ligand counterpart is present not only on endothelium but also on lymph node HEV. L-selectin appears to play a key role in homing to lymph nodes (Shimizu et al., Immunol. Today 13:106, 1992; Picker et al., Annu. Rev. Immunol. 10:561, 1992). In pathological conditions involving the immune system, it may be L-selectin that plays the most central role.

U.S. Pat. No. 5,489,578 describes sulfated ligands for L-selectin and methods of treating inflammation. The ligands are sulfooligosaccharides based on the carbohydrate structures present on the natural L-selectin ligand GlyCAM-1.

U.S. Pat. No. 5,486,536 describes the use of sulfatides as anti-inflammatory compounds. The binding activity was attributed to a critical sulfate group at position 3 on the pyranose ring of galactose. In one experiment, sulfatides were sonicated in a protein-containing buffer to produce microdroplets. The preparation was asserted to have protective effects in two animal models for acute lung injury and inflammation.

Each of the selectins shows a fine specificity in terms of the carbohydrate requirement for binding. All three selectins bind sialylated fucooligosaccharides, of which the prototype is the tetrasaccharide sialyl Lewis$^x$ (sLe$^x$). Direct binding experiments between synthetic carbohydrates and isolated selectins has permitted a more detailed dissection of the binding requirements (e.g., Brandley et al., Glycobiology 3:633, 1993). E- and L-selectin require an I2-3 linkage for the sialic acid in sLe$^x$, whereas P-selectin can recognize sialic acid in an I2-6 linkage. P-selectin also does not require a hydroxyl group in the fucose 2- and 4-positions. P- and L-selectin bind sulfated structures like sulpho-Le$^x$-(Glc)-cer and sulfatides in a manner largely independent of divalent cations, whereas E-selectin binding is exquisitely sensitive to the presence of cations. Binding of P- and L-selectin to sulfated carbohydrates is only inhibitible by other sulfated carbohydrates, whereas E-selectin does not have this requirement.

It is important to emphasize that the selectin specificity in biological reactions is mediated by much more than the carbohydrate component of the ligand. For example, P- and L-selectin (but not E-selectin) bind sulfated molecules that lack sialic acid and fucose, such as sulfatides (Aruffo et al., Cell 67:35, 1991) and certain subspecies of heparin (Norgard-Sumnicht et al., Science 261:480, 1993). For a general review of the variety of carbohydrates recognized by the selectins, see Varki et al. (Proc. Natl. Acad. Sci. USA 91:7390, 1994).

Each of the selectins has a different family of natural ligands on the surface of the opposing cell (see McEver et al., 270:11025, 1995). E-selectin binds strongly to a ligand designated ESL-1. In contrast, antibody blocking studies indicate that essentially all the binding sites for P-selectin on leukocytes are attributable to an O-glycosylated protein designated PSGL-1 (P-selectin glycoprotein ligand 1) (Moore et al., J. Cell Biol. 128:661, 1995). The natural ligands identified for L-selectin is neither of these, but include other glycoproteins with the designations GlyCAM-1, CD34, and MAdCAM-1.

The binding specificity indicates that at least two of the three selectins must be recognizing a ligand component beyond the sLe$^x$ structure. In addition to the oligosaccharide, P-selectin must bind a site on PSGL-1 with features different from ESL-1 and from other mucin-like O-glycosylated proteins, such as CD43.

A second ligand requirement for high affinity binding of the natural ligand has been identified for both P- and L-selectin. The second requirement is a sulfate residue, which is apparently not required for E-selectin binding, and has implications for the development of effective inhibitory compounds.

Imai et al. (Nature 361:555, 1993) tested the requirements for binding of L-selectin to the ligands on lymph node HEV. Radioactive inorganic sulfate is incorporated into the 50 kDa and 90 kDa glycoproteins in a manner that is inhibitible by sodium chlorate. The undersulfated glycoproteins no longer interacted in precipitation analyses with an L-selectin chimera. The inhibition experiments do not pinpoint the location of the required sulfate group to the carbohydrate or the protein backbone. Either way, the sulfate requirement distinguishes L-selectin binding specificity from that of E-selectin.

The sulfate component has been mapped more precisely in the structure of the P-selectin ligand PSGL-1. The requirement in P-selectin is provided by one or more sulfated tyrosines near the N-terminus of the polypeptide backbone, separate from the glycosylation site.

Wilkins et al. (J. Biol. Chem. 270:22677, 1995) demonstrated that PSGL-1 synthesized in human HL-60 cells can be metabolically labeled with [$^{35}$S]sulfate. It was shown that most of the $^{35}$S label was incorporated into the polypeptide in the form of tyrosine sulfate. Treatment of PSGL-1 with a bacterial arylsulfatase released sulfate from tyrosine, and resulted in a concordant decrease in binding to P-selectin.

Pouyani et al. (Cell 83:333, 1995) demonstrated that selective inhibitors of sulfation compromised binding of HL-60 cells to soluble P-selectin but not E-selectin. The cell-surface expression of sLe$^x$ or the polypeptide were not compromised by treatment. Deletion analysis of isolated PSGL-1 constructs localized the binding component to residues 20–40. The segment contains three tyrosine residues, and when these were changed to phenylalanine, P-selectin binding activity was abolished. Furthermore, when the 20 amino acid segment was fused on to a different protein, it was again sulfated during biosynthesis and had binding activity for P-selectin. These authors suggested that the sulfated tyrosines interact with P-selectin not through the carbohydrate binding domain of P-selectin, but through the EGF-like domain, which is located closer in the protein sequence to the membrane spanning domain.

Sako et al. (Cell 83:323, 1995) performed another series of binding experiments using the extracellular domain of PSGL-1 expressed as a fusion protein. The assay required fucosylation of the protein and cations in the assay medium, consistent with a dependence on carbohydrates like sLe$^x$. Mutation of the putative N-linked glycosylation sites had no effect on selectin binding, suggesting that the carbohydrate requirement was O-linked. However, mutation of three tyrosines to phenylalanine abrogated binding activity for P-selectin. Binding of E-selectin, for which PSGL-1 can also act as a ligand, was not affected by removal of the sulfation sites.

The binding affinity of P- and L-selectin for sLe$^x$ is in the mM range (Nelson et al., J. Clin Invest. 91:1157, 1993). In contrast, the affinity of P-selectin for the natural ligand is in the nM range (Moore et al., J. Cell Biol. 112:491, 1991), a difference in potency of ~10$^6$ fold. Synthetic oligosaccharides containing multiple sLe$^x$ units only partly make up the difference, so the effect is not just due to ligand valency. The disparity is also attributable to the requirement of P- and L-selectin for a strong anionic determinant, like the sulfotyrosines on PSGL-1. Compounds effective in the same concentration range as PSGL-1 must be able to supply a similarly effective determinant combination.

There is a need to develop new therapeutic compositions capable of interfering with selectin-ligand interactions, because cellular adhesion is an early event in a number of inflammatory and immunological phenomena. For systemic administration, the compositions should be effective in the nanomolar range, so that an effective amount can be given in a practicable dose. It is important to emphasize that putative compositions should be tested in a system that adequately represents the requirements of the natural interaction. A one-component inhibitor that effectively blocks a one-component interaction will typically not be effective in blocking a two-component interaction.

This disclosure describes polymerized lipid compositions that display all the features necessary to inhibit P- or L-selectin at nanomolar concentrations when tested in appropriate cell bioassays for ligand binding. Polymerized liposomes and lipid sheets have been proposed in other contexts (Spevak et al., Adv. Mater 7:85, 1995; Reichert et al., J. Am. Chem Soc. 117:829, 1995; Charych et al., Science 261:585, 1993; Charych et al., Chem. Biol. 3:113, 1996). However, the present invention is the first instance where polymerized glycoliposomes have been shown to be effective in a biological system involving the interaction of two eukaryotic cells. This is also the first instance where polymerized glycoliposomes have been shown to be an effective ligand for a binding system with a plurality of separate determinants.

SUMMARY OF THE INVENTION

The lipid compositions of this invention provide a stable scaffold from which to present a plurality of features required for ligand binding. P- and L-selectin inhibitors comprise a multivalent assembly of carbohydrates, interspersed with negatively charged lipid headgroups which are essential for activity. These compositions are proposed for use in inhibiting biological phenomena mediated by selecting, including the adherence and extravasation of neutrophils and monocytes, and the trafficking of lymphocytes through blood vessels, lymphatics, and diseased tissue.

Accordingly, certain embodiments of this invention relate to compositions for inhibiting the binding between a first cell having a P- or L-selectin and a second cell having a ligand for the selectin, comprising a sheet of lipids wherein a proportion of the lipids are covalently crosslinked, a proportion of the lipids have an attached saccharide, and a proportion of the lipids not having an attached saccharide have an acid group that is negatively charged at neutral pH. A proportion of the lipids having the attached saccharide or the acid group may be covalently crosslinked to other lipids in the sheet, and a proportion may not be ocvalently crosslinked to other lipids.

This includes embodiments wherein a proportion of the lipids in the lipid sheet have a first attached saccharide, and a separate proportion of the lipids in the lipid sheet have a second attached saccharide that is different from the first. The composition preferably has a 50% inhibition concentration (IC$_{50}$) that is 10$^2$-fold or 10$^4$-fold lower than that of monomer sLe$^x$.

Also embodied in this invention are compositions for inhibiting leukocyte adhesion or migration; compositions for inhibiting leukocyte adherence or fibrin deposition; compositions for inhibiting leukocyte adhesion or migration, compositions for inhibiting lymphocyte adhesion, and compositions for other types of interventions in cell interaction mediated by selectin, comprising inhibiting binding between a first cell having a P- or L-selectin and a second cell having a ligand for the selectin as already outlined Another embodiment of the invention is a composition for inhibiting the binding between a P- or L-selectin and a ligand for the selectin, wherein the lipid composition containing the ligands comprises a sheet of lipids wherein a proportion of the lipids are covalently crosslinked, a proportion of the lipids have an attached saccharide, and a proportion of the lipids not having an attached saccharide have an acid group that is negatively charged at neutral pH.

Also embodied is a composition for selecting polymerized glycoliposorne with selectin binding activity, comprising the steps of providing a glycoliposome with covalently crosslinked lipids, and a saccharide attached to a proportion of the covalently crosslinked lipids; introducing the glycoliposome into an environment comprising a selectin and a cell having a selectin ligand; and selecting the glycoliposome if the relative inhibitory concentration is lower than that of monomer sLe$^x$.

Also embodied is composition comprising a polymerized lipid composition in the manufacture of a medicament for use in treating a disease characterized by local alteration in the adherence of leukocytes or cancer cells to vascular endothelium, platelets or lymphatic tissue; particularly diseases of inflammatory or immunological etiology; wherein the polymerized lipid composition comprises a sheet of lipids wherein a proportion of the lipids are covalently crosslinked, a proportion of the lipids have an attached saccharide, and a proportion of the lipids not having an attached saccharide have an acid group that is negatively charged at neutral pH.

Also embodied are compositions for treating a disease characterized by local alteration in the adherence of leukocytes or cancer cells to vascular endothelium, platelets or lymphatic tissue, conprising a polymerized lipid composition comprising a sheet of lipids wherein a proportion of the lipids are covalently crosslinked, a proportion of the lipids have an attached saccharide, and a proportion of the lipids not having an attached saccharide have an acid group that is negatively charged at neutral pH. Diseases of interest include but are not limited to cardiac disease (such as ischernia reperfusion injury, myocardial infarction, myocarditis, restenosis, and deep vein thrornbosis), hemmorhagic shock, arthritis, asthma, and metastatic cancer.

Also embodied are compositions with P- and L-selectin inhibitory activity and pharmaceutical compositions prepared therefrom, as may be recited in any of the aforementioned methods or described below.

BRIEF DESCRIPTION OF THE FIGURES

In FIG. 2A the boxed panel shows the receptor ligand pairs known for L-, P- and E-selectin. They are depicted on the same cell for convenience, but participate in different ways to cell adhesion and migration. FIG. 2B is a detail showing the dual binding site model for P-selectin. In the ligand PSGL-1, the negative groups correspond to three sulfotyrosine residues. In contrast, there is no evidence for a separate anion binding site for E-selectin.

DETAILED DESCRIPTION

Figure 1:
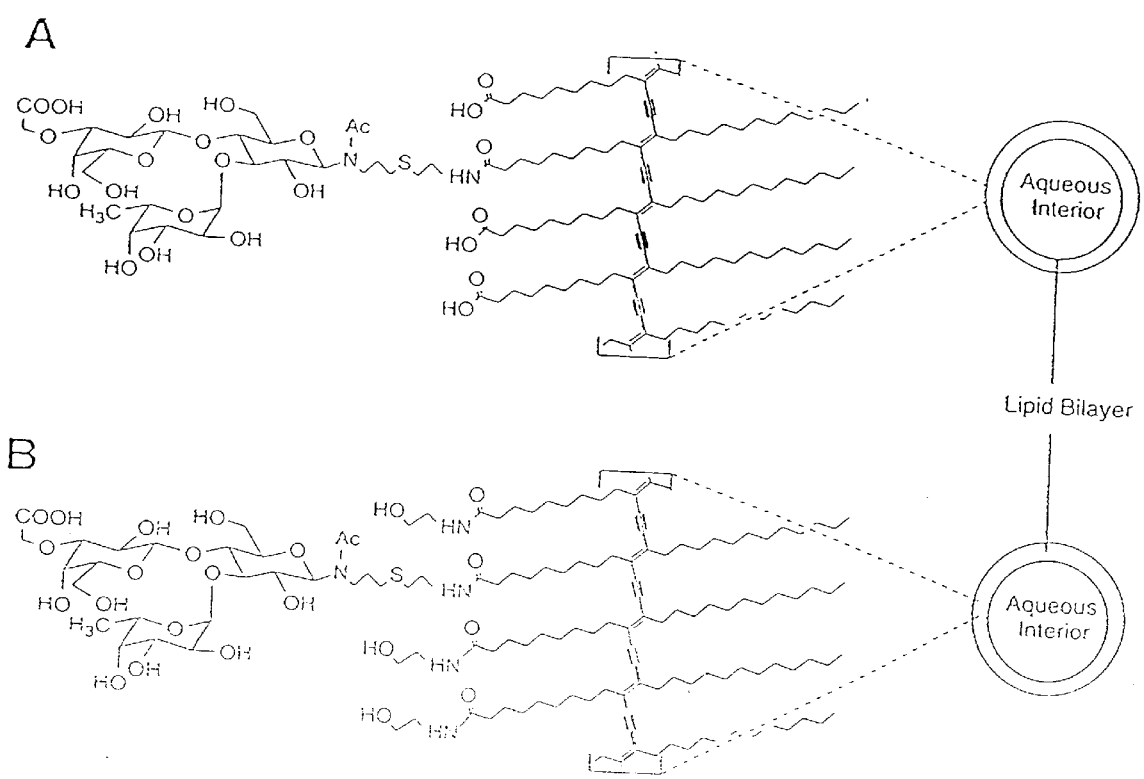
FIG. 1 is a drawing of two polymerized glycoliposomes showing an expanded detail of the chemical structure. Structure "A" is able to inhibit the binding of P-selectin to HL-60 cells at an oligosaccharide concentration below 2 nM, while Structure "B" has essentially no activity. The vesicles are unilamellar and made up of single-chain lipids with diyne groups cross-linked using UV light. Conjugated to about 5% of the lipids are analogs of the $sLe^x$ oligosaccharide. The preparations differ in terms of the outward facing determinants displayed by the neighboring lipids. In structure "A", the neighboring lipids provide carboxylic acid groups, which have a negative charge at neutral pH. In structure "B", the neighboring lipids are neutral. The negatively charged lipids work synergistically with the $sLe^x$ analog to supply P-selectin binding activity, just as sulfotyrosine works synergistically with $sLe^x$ in the natural ligand. P- and L-selectin differ from E-selectin in the requirement for a negative charge determinant in binding.
Figure 2A:
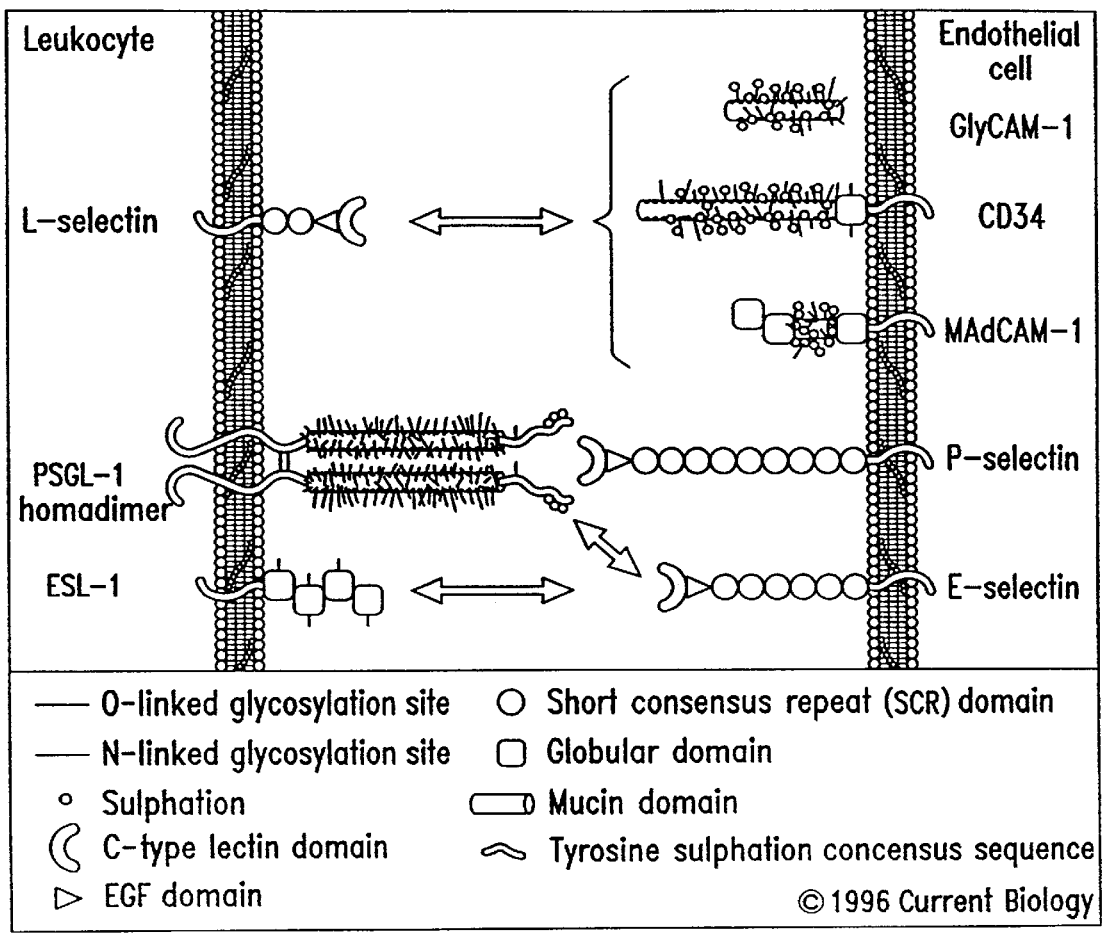
FIGS. 2A and 2B depict some of the aspects of selectin binding.
Figure 2B:
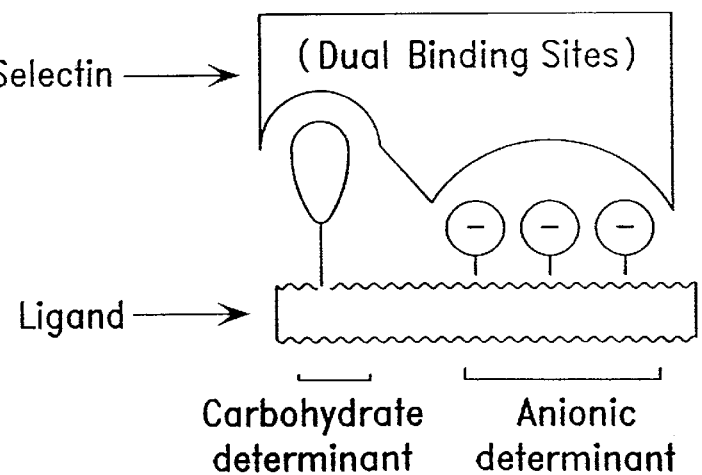

It is an object of this invention to provide a system for inhibition of the binding of P- and L-selectin to their counterpart ligands, especially during the interaction between two cells. Polymerized lipid compositions are contacted with one of the interacting cells, or else introduced into an environment where the cells are expected to interact. This type of intervention is of therapeutic interest in any circumstance where the adherence, migration, or activation of cells is mediated by a selectin, and adverse to the well-being of the host.

Polymerized glycolipid compositions for use in this invention minimally comprise three elements:

1. A stable platform made up of a lipid sheet stabilized by covalent crosslinking between a proportion of the lipids.

2. A saccharide or similar structure attached to a lipid in the lipid sheet that meets the carbohydrate binding requirement of selecting. Typically, the glycolipid is one of the crosslinked lipids in the structure, but it may instead be trapped between other lipids that form the crosslinked scaffold.

3. A negatively charged or electronegative group (usually a carboxylic acid or oxyacid) that meets the anionic binding requirement of P- and L-selectin. There is no requirement that the group play exactly the same role as the sulfotyrosines of PSGL-1, as long as the anionic binding requirement is satisfied.

When exemplary compositions were prepared and tested for inhibitory activity in a cell bioassay, a number of important observations were made that underscore the improvement provided by this technology.

Polymerized liposomes have not been tested previously for inhibition of multi-component binding. The relative positioning of the saccharide and the negatively charged group is a chance of random polymerization, not a controlled structure as it is in stepwise chemical synthesis of small molecules. It could not be predicted that an effective orientation would result, but it was found that active compositions are reproducibly produced without difficulty. New determinant combinations are easily assembled and tested for activity.

The negatively charged group of the natural ligand PSGL-1 is sulfotyrosine, and the nature of what would be required to satisfy the anionic binding requirement in liposomes was unknown. It was found that the anionic binding requirement does not require the anion to be on a protein or carbohydrate component, but can be directly coupled to lipids that become part of the lipid sheet. Surprisingly, the anionic component need not be a sulfate group, but can be provided as a simple carboxylic acid headgroup on the lipid.

The presence of the acid group on neighboring lipids unexpectedly reduced the stringency of the oligosaccharide requirement. Neutral disaccharides such as lactose and maltose have not previously been shown to have any selectin binding activity, and were included in the initial experiments as "negative controls". Unexpectedly, compositions containing these sugars and anionic lipids were potent selectin inhibitors. This is of considerable commercial interest, because the manufacture of compositions containing sugars like lactose is easier and less expensive than those containing more complex sugars such as sLe$^x$.

The inhibitory activity was remarkably high. In the cell bioassay, the sLe$^x$ analoganionic lipid combination had an IC$_{50}$ as low as 2 nM, which is up to 10$^6$-fold lower than sLe$^x$ monomer. The lactose anionic lipid combination was effective at 15 nM. This means that an effective therapeutic dose can be prepared at a lower cost and administered in a smaller volume than prior art compositions.

FIG. 1 shows exemplary lipid compositions of this invention, in which an analog of sLe$^x$ is displayed on the surface of a polymerized unilamellar liposome. Only the first structure demonstrated inhibitory activity for P-selectin binding in the bioassay, underlining the importance of the anionic component in the composition.

Because the carbohydrate and anionic determinants are on separate lipids in the polymerized lipid compositions, another benefit of the approach described here is that the components can be separately screened and titrated to produce improved compositions with refined binding characteristics.

Preparation of Polymerized Lipid Compositions

It will be readily appreciated from the drawing in FIG. 1 and the data provided in Example 2 that the practice of this invention is not critically dependent on the chemical details of the composition. Within the constraints of the three requirements above, the practitioner is free to assemble the composition according to a number of different approaches. Variations in polymerization chemistry and the conjugation of determinants are permitted and included in the scope of this invention. Designing particular linkages between a carbohydrate and a lipid is well within the skill of the ordinary practitioner. The optimization of the compounds may achieved by routine adjustment and following the effects of adjustment on selectin binding in one of many assays established in the art.

The following section is provided merely as an illustration of possible approaches for the convenience of the reader.

Preparation of components of the lipid composition: The invention uses lipids both to bear the determinants required to inhibit selectin binding, and as components for forming the lipid assemblies. Examples of lipids that can be used in the invention are fatty acids, preferably containing from about 8 to 30 carbon atoms in a saturated, monounsaturated, or multiply unsaturated form; acylated derivatives of polyamino, polyhydroxy, or mixed aminohydroxy compounds; glycosylacylglycerols; phospholipids; phosphoglycerides; sphingolipids (including sphingomyelins and glycosphingolipids); steroids such as cholesterol; terpenes; prostaglandins; and non-saponifiable lipids.

The negatively charged group of the composition is typically an acid accessible from the exterior surface of the lipid sheet. In certain embodiments, the acid is an organic acid, particularly a carboxylic acid. In other embodiments, the acid is an oxyacid of the form $(XO_n)(O^-)_p$, wherein n+p>2. In this case, the lipid will typically be of the form $R_m(XO_n)(O^-)_p$ wherein each R comprises an aliphatic hydrocarbon (which are not necessarily the same), m is 1 or 2, $(XO_n)(O^-)_p$ is an oxyacid, and n+p>2. Preferred oxyacids are sulfate, $SO_3^-$, and phosphate. A phosphate may be conjugated through one or two of its oxygens to aliphatic hydrocarbons. For any negatively charged component of the composition, any additional features may be present between the acid and the aliphatic or membrane anchoring group. These include spacers such as polyethylene glycols and other heteroatom-containing hydrocarbons. The acid group may also be present on a substituent such as an amino acid, a sugar, or a pseudo-sugar, which includes phosphorylated or sulfated forms of cyclohexidine, particularly hexaphosphatidyl inositol and hexasulfatidyl inositol.

The negatively charged group may already be present in the lipid, or may be introduced by synthesis. Examples of lipids with negatively charged headgroups include the fatty acids themselves (where the negative charge is provided by a carboxylate group), cardiolipin (phosphate groups), dioleoylphosphatidic acid (phosphate groups), and the 1,4-dihexadecyl ester of sulfosuccinic acid (sulfate group).

Negatively charged lipids not commercially available can be synthesized by standard techniques. A few non-limiting illustrations follow. In one approach, fatty acids are activated with N-hydroxysuccinimide (NHS) and 1-(3-dimethylaminopropyl)-3-ethylcarbodiimide (EDC) in methylene chloride. The leaving group N-hydroxysuccinimide can be displaced with a wide range of nucleophiles. In one example, glycine is used to yield a fatty acid-amino acid conjugate with a negatively charged headgroup. Glutamic acid can be coupled to the activated fatty acid to yield a fatty acid-amino acid conjugate with two negative charges in its headgroup. In another synthetic approach, 2,3-bis((1-oxotetradecyl)oxy)-butanedioic acid is prepared by adding myristoyl chloride in toluene to a pyridine solution of di-tartaric acid. The clarified solution is concentrated to yield the product, which is recrystallized from hexane (Kunitake et al., Bull. Chem. Soc. Japan, 51:1877, 1978).

A sulfated lipid, the 1,4-dihexadecyl ester of sulfosuccinic acid, is prepared as follows: a mixture of maleic anhydride and hexadecyl alcohol in toluene with a few drops of concentrated sulfuric acid is heated with azeotropic removal of water for 3 h. The dihexadecyl maleate is recrystallized, then heated with an equimolar amount of $NaHSO_3$ in water at 100° C. for 2–3 h. The product is recovered by evaporating the water and extracting the lipid into methanol (Kunitake et al., supra). Alkyl sulfonates may be synthesized as follows. A lipid alcohol is obtained from Sigma, or the acid group of a fatty acid is reduced to an alcohol by reacting with lithium aluminum hydride in ether to convert the carboxylate into an alcohol. The alcohol can be converted into a bromide by reaction with triphenylphosphine and carbon tetrabromide in methylene chloride. The bromide is then reacted with bisulfite ion to yield the alkyl sulfonate. Sulfates may be prepared by reacting an activated fatty acid with a sulfate-containing amine. For example, the N-hydroxysuccinimide ester of 10, 12-pentacosadiynoic acid is reacted with taurine to yield N-10, 12-pentacosadiynoyl taurine. Sulfates may also be prepared by reacting an alcohol, e.g. lauryl alcohol, with sulfur trioxide-trimethylamine complex in anhydrous dimethylformamide for 2.5 h (Bertozzi et al., Biochemistry 34:14271, 1995).

Phosphate-containing lipids not commercially obtainable are also readily synthesized. For example, to prepare dialkyl phosphate compounds, phosphoryl chloride is reacted with the corresponding alcohol. To make dihexadecyl phosphate, phosphoryl chloride is refluxed with three equivalents of hexadecyl alcohol in benzene for twenty hours, followed by recrystallization of the product (Kunitake et al., supra).

Monoalkyl phosphates may be prepared by reacting, e.g., 10, 12-hexacosadjyne-1-ol (1 eq.) with phosphoryl chloride (1.5 eq.) at ambient temperature in dry $CCl_4$ for ~12 h, then boiling under reflux for 6 h. Removal of the solvent and heating the residue with water for 1 h yields the desired 10, 12-hexacosadiyne-1-phosphate (Hupfer et al., Chem. Phys. Lipids 33:355, 1983). Alternatively, a fatty acid activated with NHS can be reacted with 2-aminoethylphosphate to yield the acylated derivative of aminoethylphosphate.

Carbohydrate components suitable for use with this invention include any monosaccharides, disaccharides, and larger oligosaccharides with selectin binding activity when incorporated into a polymerized lipid sheet. Simple disaccharides like lactose and maltose have no selectin binding activity as monomers, but when incorporated into polymerized liposomes acquire substantial activity. Accordingly, the range of suitable carbohydrates extends considerably beyond what is used in other selectin inhibitors.

In some embodiments, the carbohydrate is a disaccharide or neutral saccharide with no detectable binding as an unconjugated monomer. In other embodiments, the carbohydrates have substantial binding in the monomeric form, and are optionally synthesized as a multimeric oligosaccharide, although this is not typically required. Preferred oligosaccharides are sialylated fucooligosaccharides, particularly $sLe^x$ and $sLe^a$, analogs of sialylated fucooligosaccharides, sulfated fucooligosaccharide, particularly sulfo $Le^x$, and analogs of sulfated fucooligosaccharide. Disaccharides and larger oligosaccharide may optionally comprise other features or spacer groups of a non-carbohydrate nature between saccharide units.

A "sialylated fucooligosaccharide analog" is a saccharide that contains the minimal structural components of $sLe^x$ involved in selectin binding in a spatially similar orientation to that of $sLe^x$. These components are the 3-hydroxy group of the fucose subunit and the negatively group of the neuraminic acid subunit of $sLe^x$. In the context of L-selectin binding, preferred analogs include the 2-, 3-, and 4-hydroxy groups of the fucose subunit and the negatively charged group of the neuraminic acid subunit. The fucose and sialic acid components may be linked through a disaccharide spacer as they are in $sLe^x$, through a hydrocarbon linker (as in the tethered analogs exemplified below), or through a synthetic spacer of appropriate length containing such optional features as cyclic and aromatic groups. Exemplars of the latter type are listed in the review by Sears et al. (Proc. Natl. Acad. Sci. USA 93:12086, 1996)—see especially FIG. 7.

Figure 9:
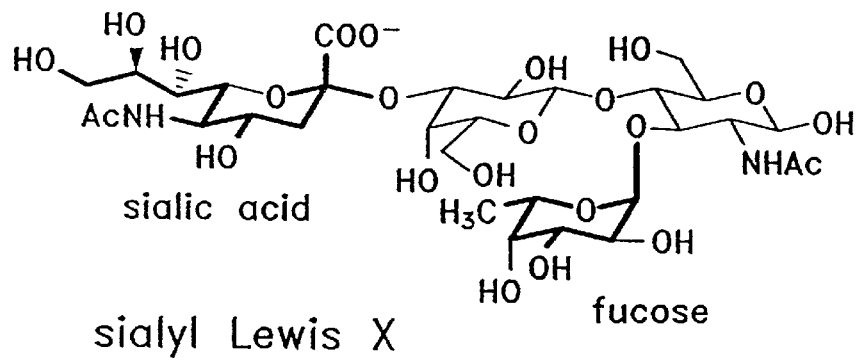
FIG. 9 is a drawing comparing the $sLe^x$ structure and an $sLe^x$ tethered analog with a novel glycoliposome comprising sialic acid and fucose residues on neighboring lipids in the crosslinked matrix.
Figure 9:
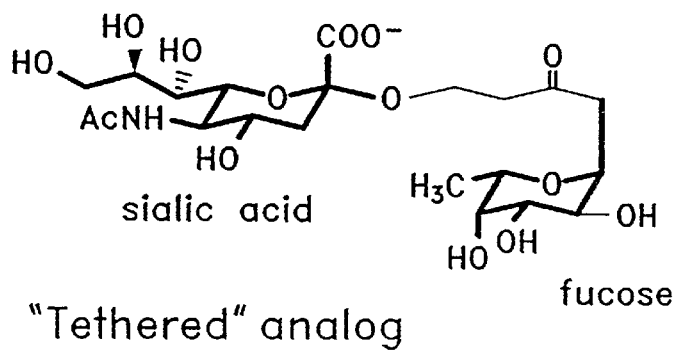
Figure 9:
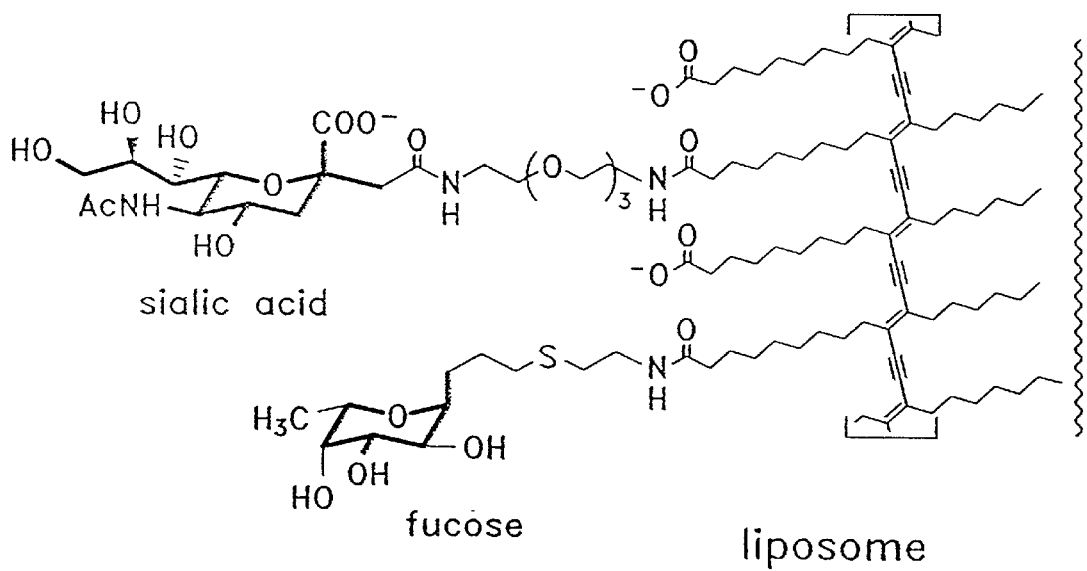

Certain analogs and other oligosaccharides of particular interest include the following: 1. Tethered disaccharides, containing a spacer between two sugars, particularly sialic acid or a sulfated form thereof and fucose, wherein the spacer is a linear or branched alkyl group (FIG. 9) or mixed hydrocarbon (Hanessian et al., J. Syn. Lett. 868, 1994). 2. Analogs comprising a fucose residue and the carboxylic acid group of sialic acid connected by hydroxylated ring structures (Lin et al., Biorganic Med. Chem. Lett 6:2755, 1996). 3. Lactose sulfated at one or more positions (Bertozzi et al., Biochemmistry 34, 14271, 1995). 4. Neutral disaccharides with an ether linkage to a carboxylic acid group (Hiruma et al., J. Am. Chem Soc. 118:9265, 1996). 5. A monosaccharide (not necessarily fucose) linked through multiple 5- or 6-member ring structures to a carboxylic acid group, at least one of the ring structures being a phenyl group (Dupre et al., Bioorg. Med. Chem. Lett., 6:569, 1996). 7. Glycopeptides, comprising a fucose or similar monosaccharide linked via a plurality of peptide bonds to a carboxylic acid (Cappi et al., Angew. Chem. Int. Ed. Engl. 1996; Wang et al., Tetrahedron Lett. 37:5427, 1996). 8. Tri- and tetrasaccharides with a plurality of sulfate groups (Nelson et al., Blood 82:3253, 1993). 9. Phosphorylated or hydroxylated cyclohexanes, particularly hexaphosphatidyl inositol and hexasulfatidyl inositol (Cacconi et al., J. Biol. Chem. 269:15060, 1994).

Many mono and disaccharides are available commercially. The syntheses of more complex carbohydrate structures for selectin binding are described extensively in the art, and need not be elaborated here. Academic articles of interest to the reader may include Tonne et al. (Tetrahedron 45:5365, 1989); Drueckhammer et al. (Synthesis 499, 1989); Hindsgaul (Sem. Cell Biol. 2:319, 1991); Look et al. (Anal. Biochem. 202:215, 1992); Ito et al. (Pure Appl. Chem. 65:753, 1993); and DeFrees et al. (J. Am. Chem. Soc. 117:66, 1995).

Conjugation of carbohydrates onto lipids can be conducted by any established or devised synthetic strategy, suitably protecting the carbohydrate during conjugation as required. One method is to react a fatty acid activated by N-hydroxysuccinimide with an amino sugar such as glucosamine or galactosamine. If an oligosaccharide-lipid conjugate is desired, the oligosaccharide may be synthesized first, utilizing an amino sugar as one of the subunits. The amino group of the amino sugar is then acylated by the activated fatty acid to yield the lipid-oligosaccharide conjugate. It should be noted that in an oligosaccharide, the amino sugar-fatty acid conjugation may interfere sterically with binding to the desired target. Thus it may be desirable to extend the oligosaccharide by interposition of other sugar subunits between the amino sugar-lipid conjugate and the portion of the saccharide acting as a ligand. For example, for $sLe^x$, the amino sugar-fatty acid conjugation may introduce steric hindrance of binding if the amino sugar is too close to the binding moieties of the $sLe^x$. Thus the $sLe^x$ should be extended by coupling the amino sugar to the GlcNAc subunit of $sLe^x$ via an O-glycosidic bond, instead of substituting the amino sugar for the GlcNAc subunit, in order to avoid steric hindrance of binding.

Another method utilizing the amino group of an amino sugar is to introduce an iodoacetyl group onto the amino group, followed by reaction of the amino group with a thiol-containing compound (such as cystamine or cysteine) which contains additional functional groups for further derivatization.

O-glycosides are readily formed by the acid-catalyzed condensation of an alcohol with monosaccharides such as glucose or mannose. N-Fmoc-ethanolamine can be added to the reducing end of glucose, followed by deprotection of the amino group with piperidine. The free amino group of the compound can then be acylated with an activated fatty acid to form a carbohydrate-lipid conjugate. Alternatively, glycosyl halides (formed by reacting a sugar with a haloacid such as HCl) can be used, where nucleophilic displacement of the halide by an alcohol forms the O-glycoside.

Another method involves the formation of N-glycosides by reacting an amine with a reducing sugar. This reaction is readily accomplished by reacting the sugar, e.g. glucose, with an amine, e.g. decylamine, at ambient temperature for ~48 h. Alternatively, heating the sugar with the amine, e.g. stearylamine (in 2–3 molar excess) at 80° C. in an ethanol/water solution will suffice to form the N-stearyl glycoside (Lockhoff, Angew. Chem. Int. Ed. Eng. 30:1161, 1991). In order to increase the stability of the N-glycoside, the product is peracetylated by stirring in 60% pyridine/40% acetic anhydride at 0° C. The peracetylated product is then dissolved in anhydrous methanol, 1M sodium methoxide is added to adjust the pH to ~10), and the mixture stirred at room temperature for 3 h to yield the N-acetyl-N-glycoside.

Figure 3:
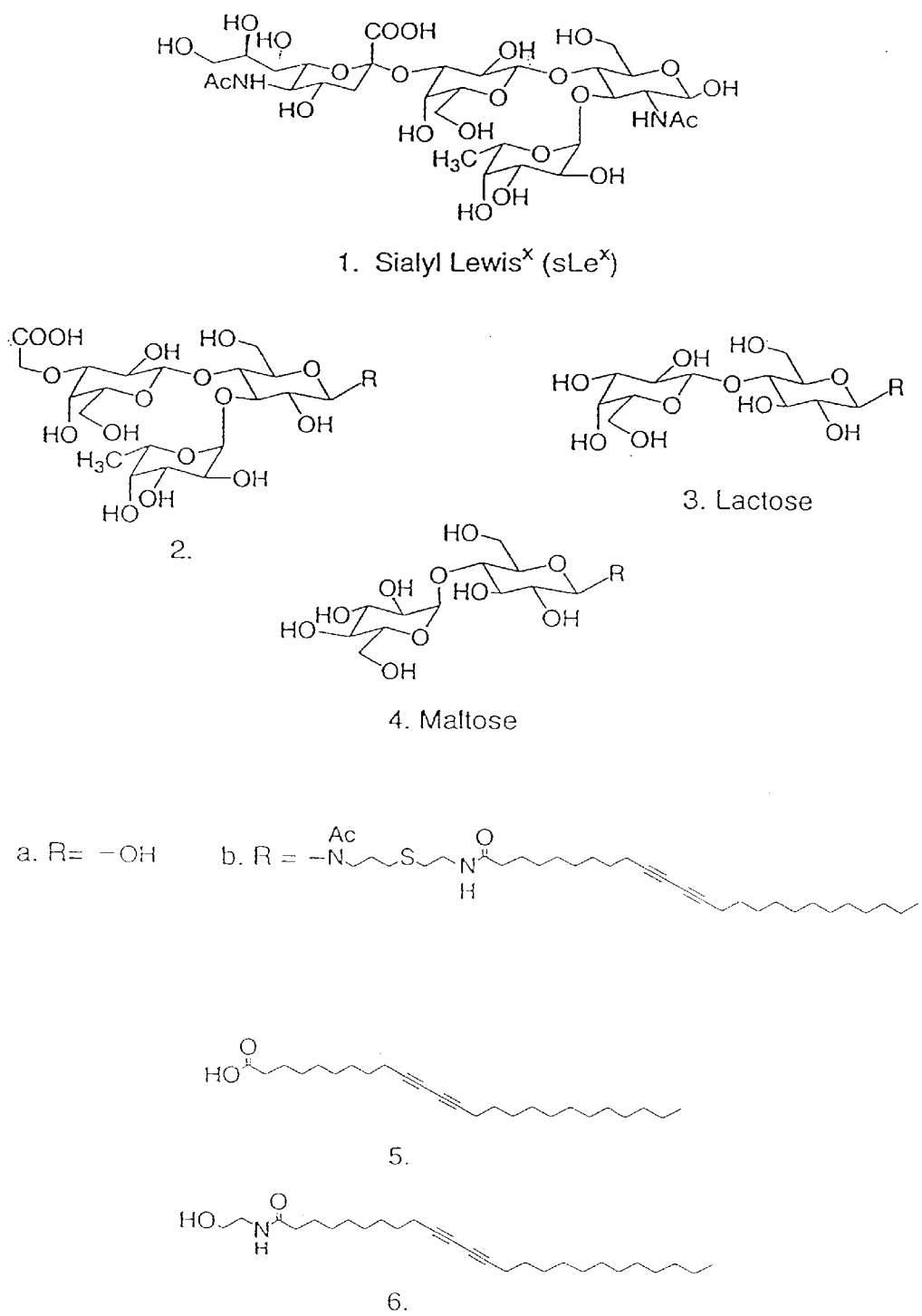
FIG. 3 is a drawing of particular components that may be chosen for assembly into glycoliposomes of this invention.

An extension of this method of introducing additional functionality via N-glycosides involves the addition of a polyfunctional amine to the sugar. For example, N-allylamine can be added to a saccharide with a free reducing end, followed by reaction of the allyl group to provide a suitable point of attachment for a fatty acid. One of skill in the art will recognize that the sugar conjugates depicted in FIG. 3 are created by reacting N-allylamine with $sLe^x$ analog, followed by peracetylation of the N-glycoside. The hydroxyl groups can be deprotected with a catalytic amount of sodium methoxide, resulting in the N-acetylated N-allyl glycoside. Alternatively, the amino group of the N-allyl glycoside can be directly acetylated with an acid chloride (Lockhoff, Angew. Chem. Int. Ed. Eng. 30:1161, 1991). A mercaptoamine such as cystamine can then be added to the N-allyl glycoside by irradiation with UV light (Roy et al., J. Chem. Soc. Chem. Comm. 1059, 1988), which results in an N-glycoside with a free amino group. The free amino group can then be readily coupled to an activated fatty acid such as the N-hydroxysuccinimide ester of 10, 12-pentacosadiynoic acid to yield the conjugated sugar.

Other methods of attaching fatty acids or other lipids to carbohydrates can be accomplished by forming suitable thioglycosides or C-glycosides. These compounds can then be further derivatized in a manner analogous to the methods used for the N-glycosides. The C-allyl glycoside of neuraminic acid, for example, is readily formed by reaction of N-acetyl mannosamine and sodium pyruvate in the presence of NeuAc aldolase as catalyst to yield N-acetyl neuraminic acid. Treatment of the crude reaction mixture with HCl gas in ethanol yields an ethyl ester; this is followed by reaction with acetyl chloride to give a glycosyl chloride (this step also results in acetylation of the hydroxyl groups). Reaction of this glycosyl chloride with allyl tributyltin and a catalytic amount of bis (tributyltin) under UV irradiation (a 450 Watt Hanovia lamp, equipped with a Pyrex filter) yields a C-allyl glycoside; the acetyl groups are then removed from the hydroxyl groups with sodium ethoxide in ethanol. This yields the ethyl ester of the C-allyl glycoside of neuraminic acid (Nagy, J. O. et al., Tetrahedron Letters 32:3953 1991).

In a manner analogous to the reaction scheme described above for the N-allyl glycosides, the C-allyl glycoside of a sugar may be reacted with cystamine, resulting in the addition of the thiol group to the allyl group, followed by reaction of the amino group with an activated fatty acid.

Conjugation of a carbohydrate to a lipid via an amide bond may be accomplished if the carbohydrate has a free carboxyl group. Mixing the carbohydrate and 2-(2-(2-(2-azidoethoxy)ethoxy)ethoxy)-ethanamine and activating the carboxyl group by using 1-(3-dimethylaminopropyl)-3-ethylcarbodiimide (EDC) and 1-hydroxybenzotriazole (HOBt) in methylene chloride, followed by reduction of the azido group to an amine with $H_2$/Pd(OH)$_2$/C in ethanol/water/dioxane/acetic acid (2:1:2:1), yields an amine-derivatized carbohydrate which can then be linked to a fatty acid by a variety of activating chemistries (Lin et al., Bioorg. & Med. Chem. Lett. 6:2755, 1996).

Carbohydrates can also be conjugated to lipids using enzymatic methods. Sugars may be transphosphatidylated by reacting diacylphosphatidyl choline and the sugar in the presence of phospholipase D, resulting in the diacylphosphatidyl-sugar (Wang et al., J. Am. Chem. Soc. 115:10487, 1993).

Assembly of the lipid composition: Appropriately derivitized lipids are combined, formed into a suitable composition, and cross-linked.

Where appropriate, the combination step includes mixing lipids having the carbohydrate requirement for selectin binding with lipids having the anionic requirement. Additional lipids can also be included for a variety of purposes. The additional lipids may have a different carbohydrate, or they may be scaffold lipids that participate in crosslinking but have no binding determinant, or they may be filler lipids that do not have crosslinking groups. Non crosslinked lipids may bear either the carbohydrate determinant, or the anionic determinant, or both, and become stabilized in the composition by entrapment between other crosslinked lipids.

The lipids are then formed into a lipid composition. Although the lipid compositions are most typically liposomes, any other arrangement can be used providing it is deliverable to the intended site of action, and displays the determinants needed for selectin binding. The participating lipids are crosslinked members of a lipid sheet, but the lipid sheet need not be part of a lipid bilayer. Micelles and microdroplets are examples of alternative particulate forms suitable for displaying the binding determinants. A single lipid sheet may also be formed about a hydrophobic core of a suitable aliphatic compound. Lipid can also be seeded as a single sheet or bilayer about another core substance, such as a protein complex. Any descriptions in this disclosure that refer to liposomes also apply to other types of lipid compositions, unless required otherwise.

Liposomes are the more usual form of the composition, because of their ease of manufacture. A number of methods are available in the art for preparing liposomes. The reader is referred to Gregoriadis (ed): "Liposome technology 2nd ed. Vol. I Liposome preparation and related techniques", CRC Press, Boca Raton, 1993; Watwe et al. (Curr. Sci. 68:715, 1995), Vemuri et al. (Pharm. Acta Helvetiae 70:95 1995), and U.S. Pat. Nos. 4,737,323; 5,008,050; and 5,252, 348. Frequently used techniques include hydration of a lipid film, injection, sonication and detergent dialysis. When using diyne chemistry and single-chain fatty acids for crosslinking, a preferred method is sonication, as described in one of the original articles (Hub et al., Angew. Chem. Int. Ed. Engl. 19:938, 1980). This method is easy to use and produces unilamellar spherical vesicles of small and uniform size. Briefly, a thin film of lipid is heated with water above 90° C., and then cooled to about 4° C., which is below the $T_c$ (Lopez et al., Biochim. Biophys. Acta 693:437, 1982) to permit the lipids to form a "solid analogous" state. The mixture is then sonicated for several minutes, with longer times (~15 min) typically producing more uniform vesicles.

After formation, the vesicles may be reduced in size, if desired, by freeze-thaw cycles or extruding through filters of progressively smaller pore size. Vesicles of any diameter are included within the scope of this invention, but they are preferably less than about 400 nm in median diameter, and more preferably less than about 200 nm in diameter. Smaller sized vesicles can be sterile-filtered and are less susceptible to uptake by phagocytic cells.

The lipids used in any of these compositions will have been prepared with fictional groups that can be covalently crosslinked once the lipid sheet is formed.

Several approaches are known in the art for covalently crosslinking lipids Polymerization may be accomplished by irradiation with ultraviolet light, or by radical initiation with compounds such as hydrogen or benzoyl peroxide, as appropriate, of lipid diynes, styrene-containing lipids, acrylic-containing lipids, and lipid dienes; polymerization (by forming amide bonds) of lipids containing free (unprotected) amino and carboxyl groups; and polymerization (by oxidation of thiol groups) of thiol-containing lipids (wherein each lipid must contain at least two thiol groups in order to be crosslinked). Azides, epoxides, isocyanates and isothiocyanates, and benzophenones also afford methods of crosslinking lipids (Wong, S. S., Chemistry of Protein Conjugation and Cross-Linking, Boston: CRC Press, 1993; Hermanson, G. T., Bioconjugate Techniques, San Diego: Academic Press, 1996).

An example of polymerization of lipids by forming amide bonds is the polymerization of N-ε-palmitoyl-L-lysine-N-β-(2-acetylamino-2-deoxy-β-glucopyranosyl)-L-asparagine by carbodiimides. The carbohydrate, lipid-modified dipeptide is readily assembled by standard solid phase peptide synthesis methods using commercially available N-α-Fmoc-N-β-(3,4,6-tri-O-acetyl-2-(acetylamino)-2-deoxy-β-glucopyranosyl)-L-sparagine (from Novabiochem) and N-α-Fmoc-N-ε-palmitoyl-L-lysine (which is readily synthesized by coupling palmitic acid activated with N-hydroxysuccinimide to the free ε-amino of commercially available N-α-Fmoc-L-lysine). Removal of the modified dipeptide from the solid-phase resin and deprotection of the fuinctional groups is carried out by standard methods. The carbohydrate, lipid-modified dipeptide can be co-polymerized with a second dipeptide, N-ε-palmitoyl-L-lysine-L-aspartic acid, in order to provide a liposome with both carbohydrate-bearing and negatively-charged groups on its surface.

An example of polymerization of lipids by oxidation of thiol groups is as follows: 10-undecenoic acid (10-undecylenic acid) is brominated by addition of HBr by Markonikov addition across the double bond, resulting in 10-bromoundecanoic acid (Streitweiser et al., Introduction to Organic Chemistry, New York: Macmillan, 1976, pp. 278–285). 10-thioundecanoic acid is prepared by treatment of 10-bromoundecanoic acid with thiourea in ethanol and subsequent hydrolysis by aqueous NaOH. (Streitweiser et al., Introduction to Organic Chemistry, New York: Macmillan, 1976, pp. 242–243). The thiol is then protected with the trityl group by heating with triphenylmethanol and boron trifluoride etherate in glacial acetic acid, followed by workup with ethanol, water, and powdered sodium acetate (Bodanszky et al., The Practice of Peptide Synthesis, New York: Springer-Verlag, 1984, p. 83). The protected thiol fatty acid is then activated with N-hydroxysuccinimide and reacted with S-trityl-L-cysteine (Novabiochem). The fatty acid-amino acid conjugate is then treated with trifluoroacetic acid to remove the trityl groups, resulting in N-(10'-thioundecanoyl)-cysteine. The dithiol can then be polymerized by oxidation with molecular oxygen.

Additional examples of lipids that can be crosslinked are reviewed in Ringsdorf et al., Angew. Chemie Int. Ed. Eng., 27:113–158 (1988), and references therein, and Johnston, D.S. et al., "Polymerized Liposomes and Vesicles," Chapter 9 in Liposome Technology, Vol. 1 (G. Gregoriadis, Ed.), Boca Raton, Fla.: CRC Press, 1984, pp. 123–129 and references therein.

A preferred method of polymerizing lipids is by polymerization of lipid diynes such as 10, 12-pentacosadiynoic acid (Farchan Laboratories, Gainesville, Fla.) by ultraviolet light. Polymerization reactions of diacetylenic compounds have been extensively studied and have been utilized in the formation of polymerized liposomes, micelles, and other supramolecular assemblies (see Frankel et al. J. Am. Chem. Soc. 113:7436, 1991; Furhop et al., J. Am. Chem. Soc. 113:7437–7439, 1991; Spevak et al., Advanced Materials 7:85, 1995). Diynes are convenient because they are easily polymerized using U.V. light, obviating the need for a radical initiator. In addition, the polymerized lipid is colored and the degree of polymerization can be easily monitored.

An example of the preparation of a crosslinkable diacyl lipid, 1, 2, 3-triamino-(bis-N1, N3-pentacosa-10, 12-diynoyl) propane, is as follows. The t-butyloxycarbonyl (Boc) group is used to protect the amino group of 2-amino-1,3-propanediol. The diol is converted into a di-mesylate with mesyl chloride, followed by immediate reaction with tetrabutylammonium azide in DMF. The azide groups are converted to amines by reaction with $PtO_2/H_2$. The compound is then reacted with the N-hydroxysuccinimide derivative of 10, 12-pentacosadiynoic acid. Finally, the Boc group is removed with trifluoroacetic acid to yield the 1N, 3N-bis (10, 12-pentacosadiynoyl)-1, 2, 3-triaminopropane.

The lipids of the composition are crosslinked by activation appropriate to the type of polymerization chemistry employed. Diyne lipids are cross-linked by U.V. irradiation as originally described (Hub et al., supra), monitoring visible absorption to follow the course of the reaction, which is usually complete by 20–60 min. Free radical initiators, where used, are removed from the preparation after polymerization by a suitable technique, such as dialysis.

Features of the Polymerized Lipid Compositions

One of the benefits of the crosslinked compositions is the ease by which different substituents can be screened and titrated for selectin binding. The optimal proportion of a particular carbohydrate determinant and a particular anionic determinant are determined empirically by titrating each substituent into the compositions and conducting a suitable selectin activity assay. This approach is illustrated further in Examples 2 and 3.

The proportion of lipids bearing a complex oligosaccharide like $sLe^x$ is preferably between about 1% and 25%, preferably about 2% to 10%, optimally about 5%. Low values probably do not provide sufficient valency, while higher values are believed to create steric problems for both polymerization and binding accessibility. The proportion of lipids bearing the electronegative determinant depends on the strength of the determinant. For many applications, there is no harm in using a hydroxyl or carboxyl lipid for the balance of the lipid in the sheet. However, stronger acids may require more care. Excessive proportion of sulfate or phosphate may confer the composition with inhibitory activity for other biological reactions, particularly those that are naturally inhibited by highly charged molecules, such as heparin. Where this is an issue, the proportion of such acids may be titrated down to a range of about 1% to 50%, or 1% to 10%, or 0.5% to 2%, as appropriate.

The degree of polymerization between lipids in the lipid sheet is a factor of the proportion of lipids having crosslinkable substituents, and the completeness of the polymerization reaction. The practitioner can limit the amount of polymerization by including lipids in the preparation that will not participate in crosslinking. While not intending to be bound by theory, it is a hypothesis of this disclosure that the synergy between the carbohydrate and anionic components is imparted partly by the rigidity of the polymerized lipid structure. It is recommended that at least 25%, preferably 50%, more preferably 75%, still more preferably 90%, even more preferably 95%, and still more preferably almost 100% of the lipids in the sheet are crosslinked. The entire sheet be polymerized into one unit, or into separate patches or tiles.

Where a proportion of non-reactive lipid is included as filler to reduce the degree of crosslinking, the carbohydrate determinant and the anionic determinant are typically on the crosslinked lipid rather than the filler lipid. However, the opposite arrangement is possible, insofar as the filler lipid will become entrapped by the neighboring crosslinks. Thus, in certain embodiments of the invention, either the carbohydrate determinant or the anionic determinant for selectin binding, or both, are provided by non crosslinked lipids present in a lipid sheet comprising other lipids that are crosslinked. This approach is especially appropriate when using glycosphingolipids to satisfy the carbohydrate determinant. Preferred lipids of this type are sulfoglucuronyl glycosphingolipids (Needham et al., Proc. Natl. Acad. Sci. USA 90:1359, 1993).

Both carbohydrate groups and electronegative groups are optionally conjugated to the lipid through a spacer group. As will already be appreciated from the synthetic methods described earlier, hydrocarbon spacers of about 2 carbons in length provide a convenient approach to conjugation. In certain embodiments, the spacer groups are polyethylene glycols that improve the stealth of the liposomes from uptake by reticuloendothelial cells. Since the anionic group and the carbohydrate group must work in concert, the length of the spacer arms should match. The potency of polymerized lipid compositions is believed to derive in part from the structural rigidity, and many embodiments have spacers of minimal length.

In certain embodiments of this invention, a proportion of the lipids in the lipid sheet have a first attached saccharide, and a separate proportion of the lipids have a second attached saccharide that is different from the first. The two glycolipids are preferably part of the cross-linked structure. Embodiments where there is a higher plurality of different independently conjugated saccharides are contemplated. Any combination of lipids in this arrangement that fulfills the carbohydrate binding requirement of selectins is suitable. In one example, the first attached carbohydrate is an acidic monosaccharide such as sialic acid or similar sugar and the second carbohydrate is fucose or similar sugar. Combinations of lipids conjugated with different monosaccharides or disaccharides or their analogs are of commercial interest because of their ease of synthesis.

Polymerized liposomes of this invention can be classified on the basis of their potency in various test assays known in the art. For example, when tested for inhibition of the binding of isolated selectin to cells expressing a selectin ligand such as PSGL-1, the liposomes preferably are able to inhibit the binding in a manner that attains 50% maximal inhibition ($IC_{50}$) at a concentration of no more than about 10 TM, preferably no more than about 1 TM, still more preferably no more than about 100 nM, and even more preferably no more than about 10 nM oligosaccharide equivalents. A preferred binding assay of this type uses HL-60 cells, and is illustrated in Example 2. Polymerized liposomes may also be categorized in any assay on the basis of the relative $IC_{50}$ compared with a suitable standard. The standard may be an oligosaccharide presented uncomplexed to liposomes or in a monomeric form, such as $sLe^x$ or $sLe^x$ analog. The standard may also be a liposome having no oligosaccharide but otherwise the same lipid composition, or a liposome made with 100% carboxy terminated or hydroxy terminated lipids. In certain embodiments, the polymerized liposomes have an $IC_{50}$ which is preferably $10^2$-fold lower, more preferably about $10^3$-fold lower, more preferably about $10^4$-fold lower, still more preferably about $10^5$-fold lower, and even more preferably about $10^6$-fold lower than that of the standard.

This invention also includes embodiments which are selective for P- and L-selectin in comparison with E-selectin, or selective for P- or L-selectin in comparison with the other two selectins. A polymerized liposome is selective if it has an $IC_{50}$ in an assay for inhibiting one selectin that is higher than its $IC_{50}$ in an assay for inhibiting another selectin. An assay is preferably used for this determination that allows the particular selectin to be the only variable. The HL-60 selectin binding assay outlined in Example 1 can be used for comparing P- and E-selectin inhibition using the same cells and switching chimeras. In a similar fashion, the plated mucin in the ELISA described in Example 3 binds a chimera of any of the three selectins, and can be used to compare the inhibitory capacity of a particular composition for all three selectins. Selective inhibitors preferably have an $IC_{50}$ that is about 5-fold higher for the target selectin in comparison with another selectin; more preferably it is 25-fold higher; still more preferably it is 100-fold higher.

Inhibitors that are selective for P- and/or L-selectin are of particular interest, because of recent observations that E-selectin antagonists can lead to conditions reminiscent of leukocyte adhesion deficiency disease (LAD-2), where neutrophils do not adhere normally to endothelial tissues, and recurrent bacterial infections of the lung, skin, and gingival tissues are common. Example 3 provides illustrations of selective polymerized liposomes. Non-sulfated sugars like $sLe^x$ and the neutral disaccharides lactose and maltose are selective for L- and P-selectin when presented in the context of carboxy-terminated lipids. $sLe^x$ is also selective in the context of hydroxyl-terminated lipids. Liposomes with sulfate groups either on sulfo $Le^x$ or on a lipid in combination with $sLe^x$ were not selective.

Also included are embodiments that are designed to optimize binding to multiple selecting. These compositions may have a plurality of different carbohydrates and a plurality of different anionic or electronegative groups on separate lipids.

Testing of the Polymerized Lipid Compositions

In vitro testing and optimization of the composition: Assays for determining the ability of a polymerized lipid composition to display selectin ligands can be classified as either direct binding assays or inhibition assays.

Direct binding assays are conducted by permitting the composition to interact directly with either a selectin or with a cell expressing a selectin. A lipid sheet containing various test selectin binding determinants can be polymerized directly onto a microscope slide (Spevak et al., Adv. Mater. 7:85, 1995) and titrated with selectin, or conversely the selectin can be coated onto microtiter plate wells and titrated with labeled polymerized lipid particles. Polymerized particles can also be tested for direct binding to cells expressing selectin ligands, such as HL-60 cells.

Since most of the applications for polymerized liposomes according to this invention relate to an inhibition of binding between selectin ligand-receptor pairs, it is more usual to develop and test compositions in inhibition assays.

Inhibition capacity can be tested in cell-free assays where one member of the selectin ligand-receptor pair is coupled to a solid surface, and the second is presented for binding in the presence of the potential inhibitor. After washing, the amount of second member bound is quantitated by way of a preattached or subsequently attached labeling system. This type of assay is convenient for comparative screening of a number of different lipid compositions, for example, displaying different carbohydrate and anionic determinants.

Many of the current cell-free selectin assay systems make use of selectin chimeras, in which an N-terminal portion of the selectin comprising the binding domain is fused to a second protein fragment that can be used as an attachment means for a labeling system. A frequently used second fragment is an IgG Fc region, which can then be detected using a conjugate made with Protein A or anti-Fc. The construction of chimeras and related assays are described by Watson et al. (J. Cell Biol. 115:235, 1992), Aruffo et al. (Cell 67:35, 1991) and Foxall et al. (J. Cell Biol. 117:895, 1992).

One illustration of a convenient cell-free assay is the L-selectin ELISA described in Bertozzi et al. (Biochemistry 34:14275, 1995). Briefly, a crude preparation of GlyCAM-1 is obtained from mouse serum. Microtiter plates are coated with polyclonal antibody specific for the peptide backbone of the mucin, overlaid with the mucin, and then washed. A chimera of L-selectin fused to Fc is complexed with biotinylated $F(ab')_2$ anti-Fc, which in turn is complexed to streptavidin-alkaline phosphatase conjugate. The combined conjugate is preincubated with the potential inhibitor for 30 min, then transferred to the microtiter plate wells. After 30 min at room temperature, the wells are washed, and developed with the enzyme substrate. In a variation of this type of assay, selectin ligand substitutes such as sulfatides are used that can be coated directly onto the plate. In another variation, the solid substrate is also a polymerized lipid (Spevak et al., Adv. Mater. 7:85, 1995) expressing determinants that are at least as potent for selectin binding as the compositions being tested as inhibitors.

Beyond the initial screening stage, one- or two-cell bioassays are preferably used during the development of compositions as being more representative of inhibition in a biological system.

A convenient one-cell assay for P-selectin inhibitors makes use of HL-60 cells, available from the ATCC. HL-60 cells naturally express the PSGL-1 antigen at about 36,000 sites per cell (Ushiyama et al., J. Biol. Chem. 268:15229, 1993). The assay is described in Brandley et al. (Glycobiol. 3:633, 1993). Briefly, an E or P-selectin chimera is incubated with biotinylated goat F(ab'), anti-human IgG Fc, and an alkaline phosphatase-streptavidin conjugate for 30 min. This complex is then incubated with potential inhibitors for ~45 min at 37° C. 50 TL of the mixture is added to each well of round-bottom microtiter plates previously blocked with BSA. An equal volume of an HL-60 cell suspension is added and the plate is incubated for 45 min at 4° C. Cells are pelleted to the well bottoms by centrifugation, washed, and developing using p-nitrophenyl phosphate.

Other one-cell assays are done with cell isolates rather than cell lines. The ability to inhibit neutrophil adhesion to purified P-selectin immobilized on plastic wells can be determined using the assay described by Geng, et al. (Nature 343:757, 1990). Briefly, human neutrophils are isolated from heparinized whole blood by density gradient centrifugation on Mono-Poly™ resolving media (Flow Laboratories), and suspended in Hanks' balanced salt solution containing $Ca^{++}$, $Mg^{++}$, and human serum albumin (HBSS/HSA). P-selectin is obtained by recombinant expression or isolated from outdated human platelet lysates by immunoaffinity chromatography on antibody S12-Sepharose™ and ion-exchange chromatography on a Mono-Q™ column (U.S. Pat. No. 5,464,935). The P-selectin is coated onto microtiter plate wells at 5 Tg/mL. Cells are added at $~2\times10^5$ per well, incubated at 22° C. for 20 min. The wells are then filled with HBSS/HSA, sealed with acetate tape, and centrifuged. After discarding nonadherent cells and supernates, the contents of each well are solubilized with 0.5% hexadecyltrimethylammonium bromide in phosphate buffer and assayed for myeloperoxidase activity (Ley et al., Blood 73:1324, 1989).

Two-cell adherence assays are conducted by testing the ability of a composition to interfere with the attachment of one cell having a selectin to another cell having a ligand for the selectin. One illustration uses COS cells transfected to express the appropriate selectin (see generally Aruffo et al., Proc. Natl. Acad. Sci. USA 84:8573, 1987). Transfected cell clones are selected for their ability to support HL-60 cell adhesion. The clones are then expanded and grown in small-well culture plates as a substrate for the assay. Another suitable substrate cell are human umbilical vein endothelial cells (HUVEC), obtainable from Cell Systems, Inc., and stimulated with 100 U/mL IL-1v for 4 h. (Martens et al., J. Biol. Chem. 270:21129, 1995). HL-60 cells are labeled by incorporation of 1 TCi/mL [$^3$H]thymidine or 10 Tg/mL calcein. The putative inhibitor is preincubated with the labeled HL-60 cells, presented to the substrate cells, and then the wells are washed and counted.

Lymphocyte adherence can be determined using the frozen section assay originally described by Stamper et al. (J. Exp. Med. 144:, 828, 1976), since modified by Stoolman et al. (J. Cell Biol. 96:722, 1988), Arbones et al. (Immunity 1:247, 1994), and Brandley et al. (supra). Briefly, lymphocytes from mouse mesenteric lymph nodes or splenocytes are fluorescently labeled with CMFDA, and incubated with the test inhibitor for ~30 min at 0° C. The lymphocyte suspension is then overlaid on 10 Tm frozen sections of mesenteric or peripheral lymph nodes ($~3\times10^4$ cells/section) and incubated on ice for 30 min on a rotator. The suspension is gently drained from the slide, and the sections are fixed with 3% glutaraldehyde and counterstained with acridine orange. Fucoidan can be used as a positive control for inhibition. The adherence observed in this assay is attributable to L-selectin binding.

Leukocyte flow (rolling cell) assays are also described in Martens et al. (supra). Neutrophils are isolated from venous blood by dextran sedimentation and Ficoll-Hypaque™ centrifugation. HUVEC are harvested by collagenase treatment, plated onto 0.1% gelatin coated flasks, and cultured. A HUVEC monolayer is mounted on the flow chamber, and perfused for 2 min with buffer containing calcium and glucose. The isolated neutrophils are preincubated with the test inhibitor in the same buffer. The neutrophil suspension is then passed over the HUVEC monolayer at a wall shear stress of $~1.85$ dyne/cm$^2$. Interaction is videotaped for about 10–20 min using a phase contrast microscope, and an imaging software program is used to determine the average number of neutrophils rolling on the monolayer in several different fields of view.

In vivo testing: Animal models for various diseases with an inflammatory or immnunological etiology are known in the art and may be brought to bear in the testing of any composition that shows promising selectin inhibitory action. In models of hyperacute disease such as reperfusion injury, the composition is typically administered within minutes or hours of the inducing event to simulate a clinical setting. In models of chronic disease, the composition is typically administered at regular periods of a week or more during the progression phase. The animal is evaluated by cellular and clinical criteria for the ability of the composition to palliate the condition.

Amongst models suitable for the testing of selectin inhibitors are the following: The cardiac ischemia reperfusion models of Weyrich et al. (J. Clin Invest. 91:2620, 1993), Murohara et al. (Cardiovasc. Res. 30:965, 1995), Ma et al. (Circulation 88:649, 1993) Tojo et al. (Glycobiology 6:463, 1996) and Garcia-Criado et al. (J. Am. Coll. Surg. 181:327, 1995); the cardiact infarct model of Silver et al. (Circulation 92:492, 1995); the pulmonary ischemia reperfusion models of Steinberg et al. (J. Heart Lung Transplant 13:306, 1994)

and Kapelanski et al. (J. Heart Lung Transplant 12:294, 1993); the cobra venom acute lung injury model and immune complex lung inflammation model in U.S. Pat. No. 5,486,536; the hemmhoragic shock model of Kushimoto et al. (Thrombosis Res. 82:97, 1996); the peritoneal exudate and endotoxin-induced uveitis models of WO 96/35418; the bacterial peritonitis model of Sharar et al. (J. Immunol. 151:4982, 1993); the meningitis model of Tang et al. (J. Clin. Invest. 97:2485, 1996); the colitis model of Meenan et al. (Scand. J. Gastroenterol. 31:786, 1996); the Dacron graft experimental thrombus model of Palabrica et al. (Nature 359:848, 1992); the tumor metastasis model of WO 96/34609; the allergic asthma model of WO 96/35418; the allergen mediated pulmonary hypersensitivity model of Gundel et al. (Am. Rev. Respir. Dis. 146:369, 1992); the diabetes models of Martin et al. (J. Autoimmunity 9:637, 1996) and Yang et al. (Proc. Natl. Acad. Sci. USA 90:10494, 1993); the model for immune complex alveolitis and dermal vasculitis by Mulligan et al. (J. Clin. Invest. 88:1393, 1991); the lymphocyte trafficking model of Hicke et al. (J. Clin. Invest. 98:2688, 1996); the IgE-mediated skin reaction model of Wada et al. (J. Med. Chem. 39, 2055, 1996); and the collagen-induced arthritis and delayed-type skin hypersensitivity models of Zeidler et al. (Autoimmunity 21:245, 1995). All the aforelisted descriptions of animal models are hereby incorporated herein by reference in their entirety.

Uses for Polymerized Liposomes

Research use: Polymerized lipid compositions of this invention can be used to characterize the nature of binding between putative ligand-receptor binding cells. For example, a newly isolated protein receptor that binds isolated neutrophils or HL-60 cells in a manner inhibitible by liposomes this invention will be suspected as a selectin. A newly isolated mucin that binds HUVEC or cells transfected with selectin in a manner inhibitible by liposomes of this invention will be suspected of being a selectin ligand. Adhesion or activation of one cell by another in a manner inhibitible by liposomes of this invention will be suspected of being mediated by selectin-ligand coupling.

Diagnostic use: Polymerized lipid compositions can also be used for the detection of human disorders in which the ligands for the selectins might be defective. Such disorders would most likely be seen in patients with increased susceptibility to infections involving an abnormality in leukocyte migration or lymphocyte activation.

For in vitro diagnostic procedures, cells to be tested are collected from blood, separated by Ficoll-Hypaque™ centrifugation, and then tested for their ability to bind a polymerized liposome with selectin binding activity. The liposome may be labeled with a radioisotopic or fluorescent marker, or if based on diyne chemistry, monitored by way of its intrinsic color. Direct binding of the composition to the cells can provide a measure of selectin on the cell surface. In one illustration, T cells or cells dispersed from a tumor biopsy are isolated and the composition is used to measure the density of selectin. In another illustration, the composition is used in a mixed leukocyte population to count the number of cells expressing selectin.

For in vivo diagnostic procedures, the lipid composition is labeled by conjugation with or encapsulation of a suitable agent. Radioisotopes such as $^{111}$In or $^{99m}$Tc can be used as labels for scintigraphy, or non-radioactive dense atoms can be used to enhance x-ray contrast. The composition is administered intravenously at a peripheral site or via local intubation. Abnormal localization at a particular site may reflect unusual cell trafficking or activation with clinical implications.

Therapeutic use: Since the selectins have several functions related to leukocyte adherence, inflammation, and coagulation, compounds that interfere with binding of P-selectin or L-selectin can be used to modulate the pathological consequences of these events.

An inflammatory response can cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial necrosis despite restoration of blood flow. Reperfusion injury is known to be associated with adherence of leukocytes to vascular endothelium in the ischemic zone, presumably in part because of activation of platelets and endothelium by thrombin and cytokines that makes them adhesive for leukocytes (Romson et al., Circulation 67:1016, 1983). The adherent leukocytes can migrate through the endothelium and destroy ischemic myocardium just as it is being rescued by restoration of blood flow. Ischemia may occur pursuant to a myocardial infarction or as a result of complications of surgery, such as deep vein thrombosis. Another inflammatory condition of concern in cardiology is restenosis.

There are a number of other common clinical disorders in which ischemia and reperfusion results in organ injury mediated by adherence of leukocytes to vascular surfaces, including strokes; mesenteric and peripheral vascular disease; organ transplantation; and multiple organ failure following circulatory shock. Bacterial sepsis and disseminated intravascular coagulation often exist concurrently in critically ill patients. These conditions are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Tumor cells from many malignancies (including carcinomas, lymphomas, and sarcomas) metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers. It has been reported that P-selectin binds to tumor cells in human carcinoma tissue sections and cell lines derived from carcinomas (Aruggo et al., Proc. Natl. Acad. Sci. USA 89:2292, 1992). In addition, certain tumors may themselves express selectins or selectin ligands, which may participate in the adherence of metastasizing cells to endothelial cells or HEV at a new site.

Antagonists of P-selectin may be beneficial for blocking platelet-leukocyte interaction as thrombi develop (Welpy et al., Biochim. Biophys. Acta 117:215, 1994). In baboons, administration of anti P-selectin decreased fibrin deposition into Dacron graft implants without diminishing platelet accumulation into the grafts (Palabrica et at., Nature 359, 848, 1992). The results suggest that the trapping of leukocytes, via interaction with platelets, may contribute to the deposition of fibrin. Blocking P-selectin should prevent this interaction and nay have value as an anti-thrombogenic therapy.

To the extent that the initiation of an acute allograft or xenograft rejection involves selectin-mediated recruitment of inflammatory or immune mediator cells, selectin antagonists can be brought to bear in the few days after engraftment.

Antagonists of P- and L-selectin are also of interest in palliating autoimmune diseases. For a review of the role of adhesion molecules in these diseases, the reader is referred to Murray (Sernin. Arthritis Rheum. 25:215, 1996).

Rheumatoid arthritis is characterized by symmetric, polyarticular inflammation of synovial-lined joints, and may involve extraarticular tissues, such as the pericardium, lung, and blood vessels. Adhesion molecules appear to play an important role (Postigo et al., Autoimmunity 16:69, 1993). Soluble selectins are present in the synovial fluid and blood of affected patients, correlating with elevated ESR and synovial PMN count (Carson CW et al. J. Rheumatol. 21:605, 1994). Conventional antirheumatic therapy may modify synovial inflammation by altering leukocyte adhesion. Corticosteroids, gold compounds, and colchicine downregulate endothelial expression of selectins (Corkillet al, J. Rheumatol. 18:1453, 1991; Molad et al, Arthritis Rheum. 35:S35, 1992).

Systemic lupus erythematosus is characterized by formation of antinuclear antibodies and manifest by inflammatory lesions on the skin and throughout the body. Selectin expression is increased on dermal vessel endothelial wall of patients with increased disease severity (Belmont et al., Arthritis Rheum. 37:376, 1994). Sjoren's syndrome, autoimmune thyroid disease, multiple sclerosis, and diabetes are other conditions with a heavy implication of altered adhesion proteins such as ICAM-1, LFA-1 and -3, VCAM-1, and selectins (Murray, supra), and may be amenable to therapy with selectin inhibitors.

Asthma is characterized by airway obstruction, inflammation, and increased responsiveness to a variety of stimuli, manifest by episodes of cough, dyspnea and wheezing The steps proposed in chronic airway inflammation include inflammatory stimulus triggering release of mediators, followed by activation of the leukocyte-endothelial adhesion cascade resulting in leukocyte adhesion to the endothelium. Adhesion molecules implicated include selectins, VCAM-1, and ICAM-1 which may be up-regulated following allergen challenge (Pilewski et al., Am. Rev. Respir. Dis 148, S31, 1993).

Timing and objectives of treatment. An effective amount of polymerized lipid compositions may be used for treating an individual for condition wherein etiology involves altered cell traffic or activation, mediated in part by selectins.

An "individual" treated by the methods of this invention is a vertebrate, particularly a mammal (including farm animals, sport animals, and pets), and typically a human.

"Treatment" refers to clinical intervention in an attempt to alter the natural course of the individual being treated, and may be performed either for prophylaxis or during the course of clinical pathology. Desirable effects include preventing occurrence or recurrence of disease, alleviation of symptoms, diminishment of any direct or indirect pathological consequences of the disease, such as hyperresponsiveness, inflammation, or necrosis, preventing metastasis, lowering the rate of disease progression, amelioration or palliation of the disease state, and remission or improved prognosis. The "pathology" associated with a disease condition is anything that compromises the well-being, normal physiology, or quality of life of the affected individual.

Treatment is performed by administering an effective amount of a polymerized lipid composition of this invention. An "effective amount" is an amount sufficient to effect a beneficial or desired clinical result, and can be administered in one or more doses.

The modes of treatment contemplated in this invention include but are not limited to the following:

1. Inhibiting leukocyte adhesion or migration, comprising administering a P-selectin inhibitor so as to inhibit binding between a vascular endothelial cell and a leukocyte selected from the group consisting of neutrophils, monocytes, eosinophits, and lymphocytes bearing a P-selectin ligand, thought to be memory T cells. The inhibiting can be performed either by introducing the inhibitor into an environment where the interacting cells come into contact, particularly near the affected site, or contacting the cell bearing the selectin with the inhibitor in the absence of the cell bearing the ligand.

2. Inhibiting platelet aggregation or fibrin deposition by administering a P-selectin inhibitor to an environment containing platelets or susceptible of accumulating platelets.

3. Inhibiting leukocyte adhesion or migration, comprising administering an L-selectin inhibitor so as to inhibit binding between a lymphocyte, neutrophil or monocyte and an endothelial cell or lymphatic tissue, particularly an HEV cell.

4. Inhibiting lymphocyte adhesion, migration, or activation, comprising administering an L-selectin inhibitor to the lymphocyte.

5. Inhibiting metastasis of a tumor suspected of expressing a selectin ligand or receptor by administering an inhibitor for the selectin to the tumor or to the circulation.

The criteria for assessing response to therapeutic modalities employing the lipid compositions of this invention are dictated by the specific condition, For example, the treatment to prevent extension of myocardial infarction can be monitored by serial determination of marker enzymes for myocardial necrosis, and by EKG, vital signs, and clinical response. Treatment of acute respiratory distress syndrome can be monitored by following arterial oxygen levels, resolution of pulmonary infiltrates, and clinical improvement as measured by lessened dyspnea and tachypnea. Other conditions treated using the methods of this invention are measured according to standard medical procedures appropriate for the condition.

Pharmaceutical preparations and administration: Compositions prepared for use according to this invention can be prepared for administration to an individual in need thereof, particularly humans, in accordance with generally accepted procedures for the preparation of pharmaceutical compositions. Preferred methods for preparing liposomes described herein are sufficiently flexible that batch sizes from 5 mL to several liters or more can be prepared reproducibly and under sterile conditions.

General procedures for preparing pharmaceutical compositions are described in Remington's Pharmaceutical Sciences, E. W. Martin ed, Mack Publishing Co., Pennsylvania. Liquid pharmaceutically administrable compositions can, for example, be prepared by dispersing a liposome in a liquid excipient, such as water, saline, aqueous dextrose, or glycerol. The liposome suspension may include lipid-protective agents to protect lipids against free-radical and lipid-peroxidative damages on storage. Lipophilic free-radical quenchers, such as alphatocopherol and water-soluble iron-specific chelators, such as ferrioxarnine, can be used. One of the advantages of the polymerized lipid compositions of the present invention is stability against many of the usual degradative effects that accumulate upon storage. The composition may optionally also contain other medicinal agents, pharmaceutical agents, and carriers.

Compositions for injection can be supplied as liquid solutions or suspensions, or as solid forms suitable for dissolution or suspension in liquid prior to injection. For administration to the trachea and bronchial epithelium, a preferred composition is one that provides either a solid or liquid aerosol when used with an appropriate aerosolizer device. Although not required, pharmaceutical compositions are in some instances supplied in unit dosage form suitable for administration of a precise amount.

The route of administration of a pharmaceutical composition depends, inter alia, on the intended target site, clinical condition, and the nature of the condition being treated. Intravenous or intraly mphoid administration or injection directly into an affected site are the most usual routes. Pulmonary administration by aerosol is conducted using a nebulizer device. Apparatus and methods for forming aerosols are described in Kirk-Othmer, "Encyclopedia of Chemical Technology", 4the Ed Vol. 1, Wiley N.Y., pp. 670–685, 1991.

The size of the dose is selected taking into account the expected volume of distribution of the composition before reaching the intended site of action, and then providing sufficient inhibitor (in nM sugar equivalent) to meet or exceed the $IC_{50}$ concentration as measured in an appropriate cell bioassay, typically at about 2–20 times $IC_{50}$ concentration. In planning the dose, it may not be necessary to completely block all of the selectin receptors. For normal healing, at least some leukocytes may need to migrate to the affected site. The amount of inhibitor is adjusted accordingly.

The assessment of the clinical features and the design of an appropriate therapeutic regimen for the individual patient is ultimately the responsibility of the prescribing physician.

The foregoing description provides, inter alia, a detailed explanation of how polymerized lipid compositions can be used to inhibit cellular events mediated by selectin binding. It is understood that variations may be made with respect to structure of the composition or its implementation without departing from the spirit of this invention.

All patents, patent applications, articles and publications mentioned herein, both supra and infra, are hereby incorporated herein by reference in their entirety.

The examples presented below are provided as a further guide to a practitioner of ordinary skill in the art, and are not meant to be limiting in any way.

EXAMPLES

Example 1
Development of Two-Component Glycoliposomes

Glycoliposomes were formed by attaching a carbohydrate component to a polymerizable lipid, mixing with a second polymerizable lipid with a polar head group, forming liposomes, and then polymerizing the lipids.

FIG. 3 shows the sialyl Lewis$^x$ (sLe$^x$) tetrasaccharide (structure 1) in comparison with the components assembled into liposomes. The carbohydrates labeled as 2a (an sLe$^x$ analog), 3a (lactose), and 4a (maltose) were used for synthesizing the polymerizable glycolipids, hereafter designated as 2b, 3b and 4b, respectively. The precursor polymerizable lipid was 10,12-pentacosadiynoic acid (PDA), which was conjugated to the carbohydrate by standard techniques. The second polymerizable lipid used during liposome formation was either compound 5 (PDA), which comprises a negatively charged headgroup, or compound 6, which comprises a polar but uncharged headgroup.

FIG. 1 depicts an expanded view of polymerized glycoliposomes, containing either compounds 2b and 5(A) or 2b and 6(B). The polymerized glycoliposomes were formed as follows: Various molar percentages of lipids were prepared so as to give 1 mM solutions in total lipid while varying the percentages of glycolipids in the range 0.5 to 50%. The glycolipids were formed into liposomes by the probe sonication method (R.R.C. New, pp. 33–104, in "Liposomes: a practical approach", Oxford U. Press 1990). The lipids appeared to be miscible based on an analysis of their Langmuir isotherms (G. L. Gaines, in "Insoluble monolayers at liquid-gas interfaces", Wiley:N.Y. 1966).

Polymerization of the liposomes was carried out by exposure of the aqueous solutions to UV light at 254 nm (Hub et al., Angew. Chem. Int. Ed. Engl. 19:938, 1980; Spevak et al., J. Amer. Chem. Soc. 115:1146, 1993). Polymerization of lipid diacetylenes requires the monomers to adopt a solid analogous state. The carbohydrate percentages reported here are estimates of the sugar groups appearing on both the inner and outer liposome surfaces. With percentages of the glycolipid component above approximately 40%, polymerization was substantially inhibited. This is rationalized by the steric crowding of adjacent carbohydrate headgroups which prevent the proximal diacetylenes from polymerizing.

Characterization of the polymerized glycoliposomes by transmission electron microscopy (TEM) showed that the preparation consisted of spheres between 20–100 nm in diameter.

Example 2
Bioassay for Selectin Inhibition Activity

Ability of the compositions prepared in Example 1 to inhibit selectin binding was tested in a standard bioassay. The assay for measuring P-selectin binding to HL-60 cells was taken from the description in Brandley et al. (Glycobiol. 3:633, 1993). Briefly, P-selectin chimera is allowed to form a complex with biotinylated goat F(ab') anti-human IgG Fc and alkaline phosphatase-streptavidin, and is preincubated with inhibitors before mixing with HL-60 cells. The cells were pelleted by centrifugation and washed with TBS. Chromagen was added and the color that developed was read as an OD at 405 nm. All assays were run in quadruplicate.

Figure 4:
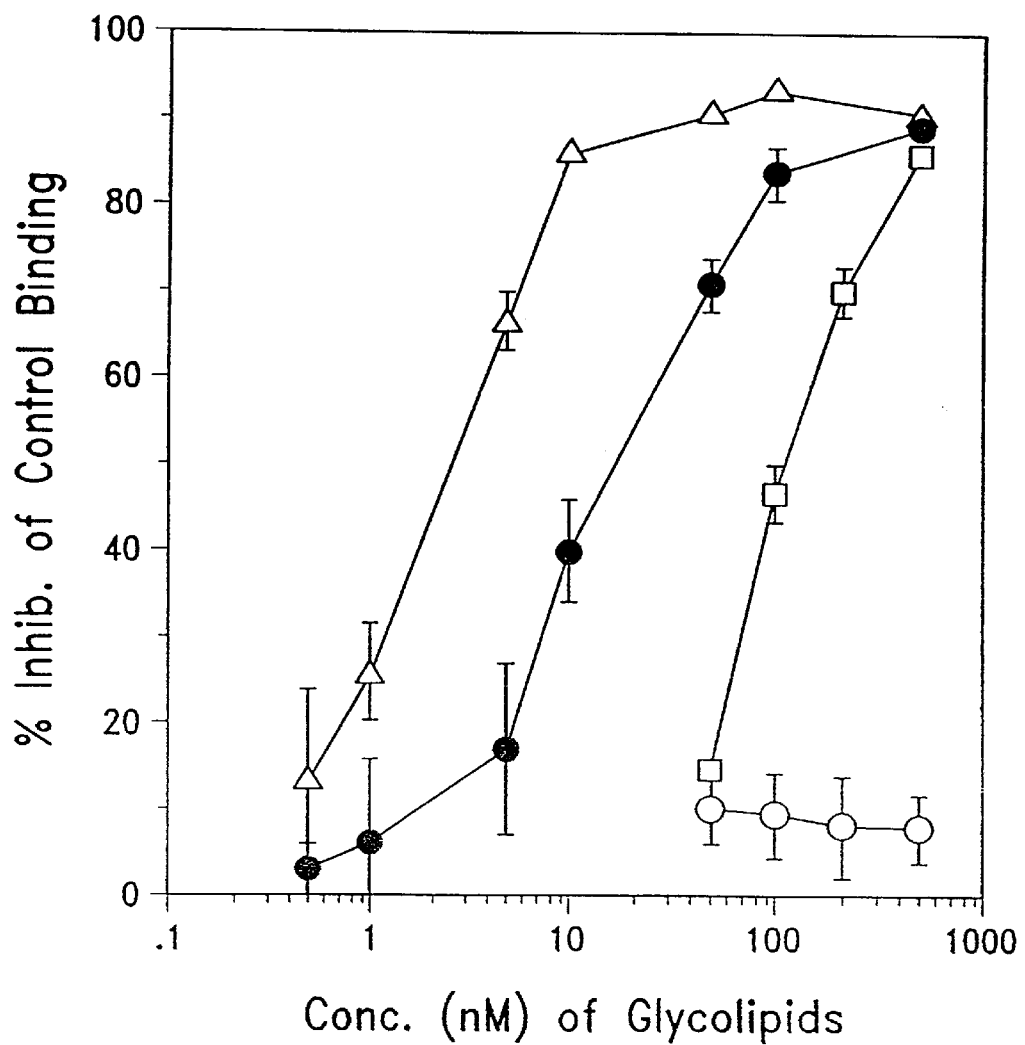
FIG. 4 is a titration curve for the inhibition of P-selectin binding to HL-60 cells by glycoliposomes. In order of decreasing potency (left to right) the compositions are comprised of: $sLe^x$ analog plus acidic lipids; lactose plus acidic lipids; maltose plus acidic lipids; and $sLe^x$ analog plus neutral lipids.

FIG. 4 shows the inhibition titration curve for various polymerized glycoliposome preparations containing 5% carbohydrate-linked lipid. Open triangles: sLe$^x$ analog conjugate plus acidic lipids. Open circles: sLe$^x$ analog conjugate plus neutral lipids. Closed circles: lactose conjugate plus acidic lipids. Squares: maltose conjugate plus acidic lipids. It is evident from the results of this assay that the presence of the acidic lipid is critical for measurable inhibition, even when the most effective carbohydrate conjugate of those tested, the sLe$^x$ analog, is used. The neutral disaccharides lactose and maltose also have selectin inhibition activity when used alongside acidic lipids. All the compositions having a saccharide and a negatively charged lipid inhibited P-selectin binding in a dose-dependent fashion.

Figure 5A:
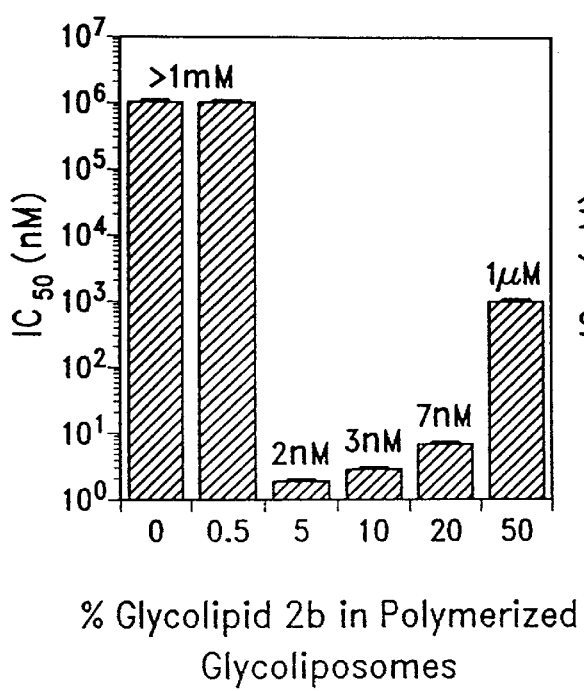
FIGS. 5A and 5B are bar graphs showing the 50% inhibition concentration of various glycoliposome preparations.
Figure 5B:
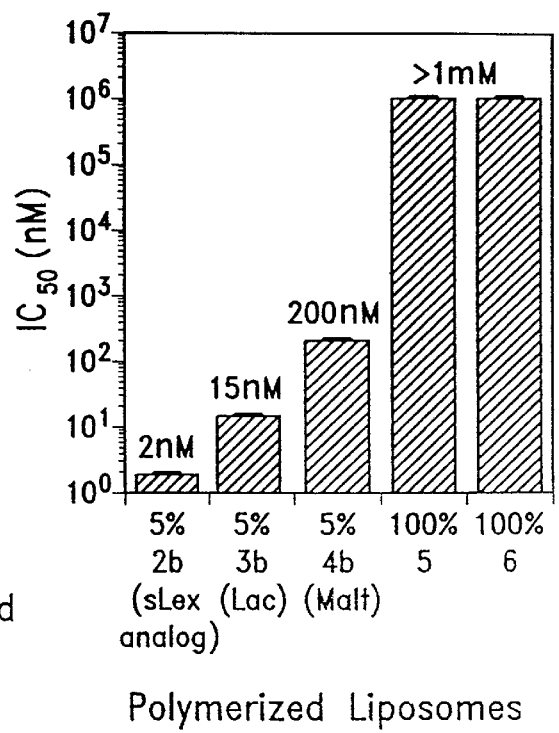

FIGS. 5A and 5B show the concentration giving 50% inhibition ($IC_{50}$) for various polymerized glycolipid compositions. The $IC_{50}$ values are based on the total concentration of glycolipid. No reduction was made for any glycoside that may be inaccessible due to incorporation into the inner layer of the liposome. Therefore, these $IC_{50}$ values represent an upper limit of the actual glycoside available for binding.

FIG. 5A is a titration analysis of the optimal proportion of carbohydrate lipid to total lipid in the composition. This experiment was conducted with the $sLe^x$ analog lipid conjugate, with the balance of the composition being the lipid having the carboxylic acid headgroup. It is evident that the optimal percentage is about 5%, although compositions up to at least 50% contain inhibitory activity, and compositions up to about 20% have inhibitory activity in the nM range. The decrease in inhibitory activity at the higher percentages correlates with the increased difficulty in polymerizing these compositions, which is attributed to steric hindrance by the carbohydrate. The 2 nM $IC_{50}$ for the 5% composition contrasts by about 1 to $5 \times 10^6$ with values obtained in this assay for $sLe^x$ monomer.

FIG. 5B is a comparison of the $IC_{50}$ for various compositions with different carbohydrate constituents. Both lactose and maltose provide significant inhibitory activity (15 nM and 200 nM respectively) when provided in the context of acidic lipids. The value for lactose in particular compares favorably with that for $sLe^x$ compositions. The last two bars show the lack of detectable inhibition by polymerized liposomes made with acidic or neutral lipids alone.

Thus, both a suitable carbohydrate and a separate negatively charged lipid are required in these preparations to provide selectin inhibition activity. In hindsight, we speculate that the binding of other inhibitory compounds, such as certain types of heparin, inositol hexakis phosphate, sulphoglucuronyl glycolipids, fucoidan, sulfatides and an $sLe^x$-RGD conjugate, can be explained as a combination of a carbohydrate or carbohydrate-like molecules and separately spaced multiple acid groups.

The possibility of intercalation of the liposomes into the cells, thereby effecting their ability to bind P-selectin, was also addressed. The cells were pretreated with the liposomes and washed to remove the liposomes prior to the addition of the P-selectin chimera. This did not result in any reduction in selectin binding to the cells. The inhibition was unaffected in experiments where the reagents and inhibitors were added simultaneously to the microtiter plates.

By way of comparison, the level of $sLe^x$ or $sLe^x$ analog presented as a monomer required to reach $IC_{50}$ in this assay is ~1 to 5 mm. The relative improvement imparted by incorporation in the polymerized liposome is approximately $10^6$-fold.

Example 3
Further Confirmation of the Requirement for Negatively Charged Lipids

Additional polymerized glycoliposome compositions were prepared for testing in a different assay system.

The assay is an ELISA in which the polymerized liposomes are tested for an ability to inhibit the binding of selectin chimera to isolated GlyCAM-1. A full description is provided in Bertozzi et al. (Biochemistry 34:14275, 1995). Briefly, a crude preparation of GlyCAM-1 is obtained from mouse serum by extraction with 2:1 chloroform/methanol, recovery of the aqueous phase, and concentration. This mucin acts in this assay as a ligand for any of the three selecting. Microtiter plates are coated with polyclonal antibody specific for the peptide backbone of the mucin, overlaid with the mucin, and then washed. Meanwhile, a complex is formed between: a) a chimera of the respective selectin fused to the Fc region of the human IgG heavy chain; b) biotinylated $F(ab')_2$ anti-Fc; c) streptavidin-alkaline phosphatase conjugate. This solution (70 TL) is combined with 70 TL of inhibitor and incubated for 30 min, then transferred to the microtiter plate wells. After 30 min at room temperature, the wells are washed, and developed with the enzyme substrate p-nitrophenyl phosphate.

Figure 6A:
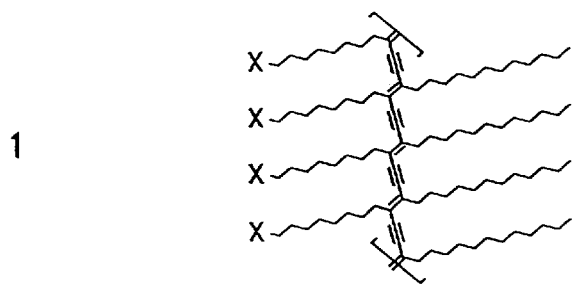
FIGS. 6A through 6E are drawings of polymerized liposomes tested for binding in Example 3. Amongst the components tested, the sulfo $Le^x$ analog was found to be the best carbohydrate, and lipid with a sulfate group best fulfilled the requirement for a separate negatively charged group.
Figure 6B:
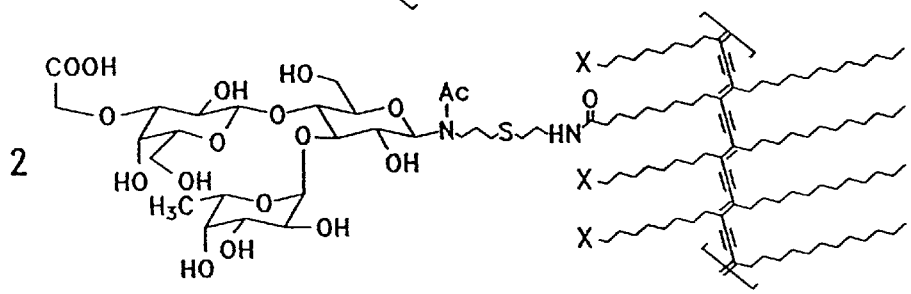
Figure 6C:
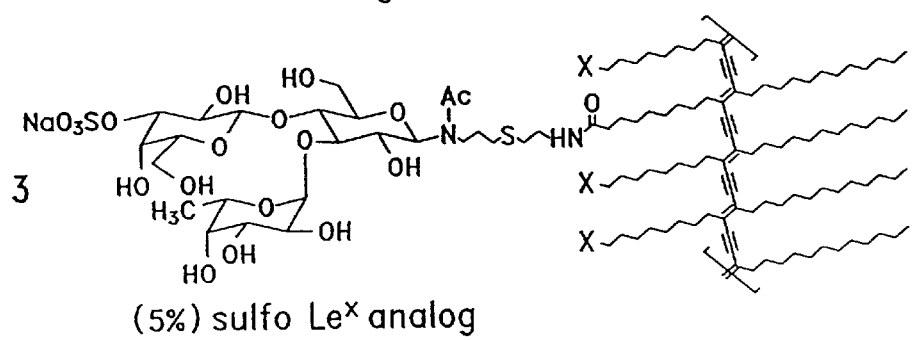
Figure 6D:
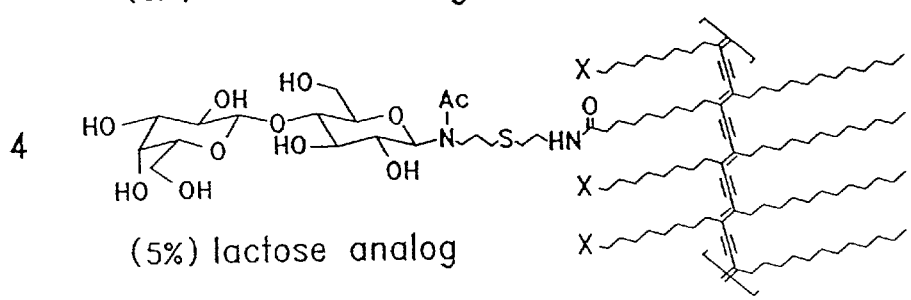
Figure 6E:
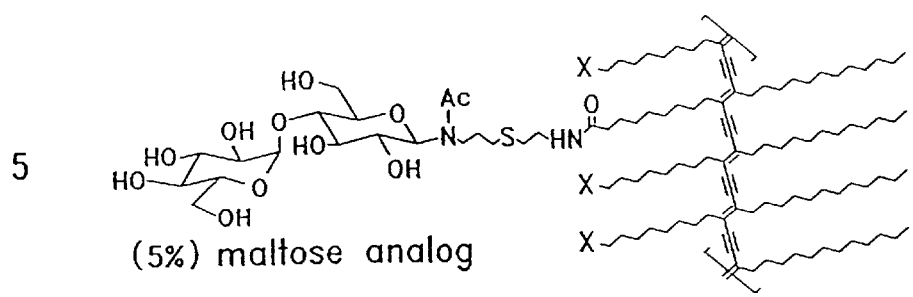

FIGS. 6A and 6B show the polymerized liposomes prepared for testing. Five different groups were prepared having either no oligosaccharide (Group 1, depicted in FIG. 6A), or one of four different oligosaccharide conjugated lipids at a relative molar concentration of 5% (Groups 2–5, depicted in FIGS. 6B–6E respectively). Within each group, the substituent on the lipids not conjugated with oligosaccharide (shown as an "X" in the diagram) was varied as follows:

an amine, which has a positive charge at neutral pH;

a hydroxyl group, which is neutral but electronegative;

a carboxylic acid, which has a negative charge at neutral pH; or a mixture comprising either 5% or 50% lipid with the oxyacid sulfate, the balance being lipid with a hydroxyl head group.

These compositions gave the following results in the selectin inhibition assay:

TABLE 1

Selectin Inhibition of Polymerized Glycoliposomes

| Group | Carbohydrate lipid substituent | Other lipid substituent | Inhibitory Activity $IC_{50}$ in TM | | |
|---|---|---|---|---|---|
| | | | L-selectin | E-selectin | P-selectin |
| 1 | (none) | —$CONHCH_2CH_2NH_2$ | >250 | >250 | >250 |
| | | —$CONHCH_2CH_2OH$ | >250 | >250 | >50 |
| | | —COOH | >250 | >250 | >100 |
| | | —$CONHCH_2CH_2OSO_3$— —$CONHCH_2CH_2OH$(5:95) | >250 | >250 | 18 |
| | | —$CONHCH_2CH_2OSO_3$— —$CONHCH_2CH_2OH$ (50:50) | 7.5 | >50 | 4.4 |
| 2 | 5% $sLe^x$ analog | —$CONHCH_2CH_2NH_2$ | >12.5 | >12.5 | >12.5 |
| | | —$CONHCH_2CH_2OH$ | 1.12 | >12.5 | 1.5 |
| | | —COOH | 0.50 | >2.5 | 0.47 |

TABLE 1-continued

Selectin Inhibition of Polymerized Glycoliposomes

| Group | Carbohydrate lipid substituent | Other lipid substituent | Inhibitory Activity $IC_{50}$ in TM | | |
|---|---|---|---|---|---|
| | | | L-selectin | E-selectin | P-selectin |
| | | —CONHCH$_2$CH$_2$OSO$_3$—<br>—CONHCH$_2$CH$_2$OH (50:50) | 0.26 | 0.45 | 0.18 |
| 3 | 5% sulfo Le$^x$ analog | —CONHCH$_2$CH$_2$NH$_2$ | >12.5 | >12.5 | >12.5 |
| | | —CONHCH$_2$CH$_2$OH | 0.26 | 0.38 | 0.18 |
| | | —COOH | 0.26 | 0.68 | 0.28 |
| | | —CONHCH$_2$CH$_2$OSO$_3$—<br>—CONHCH$_2$CH$_2$OH (50:50) | 0.20 | n.d. | n.d. |
| 4 | 5% lactose | —CONHCH$_2$CH$_2$OH | >12.5 | >12.5 | >12.5 |
| | | —COOH | 1.80 | >12.5 | 0.50 |
| 5 | 5% maltose | —CONHCH$_2$CH$_2$OH | >12.5 | >12.5 | 3.0 |
| | | —COOH | 3.0 | >12.5 | 1.3 |

The $IC_{50}$ values are all based on the total amount of liposome bound carbohydrate except in Group 1, where the values are calculated from the total amount of matrix head groups.

The results support the following conclusions. First, the sulfated carbohydrate sulfo Le$^x$ analog has a very low $IC_{50}$ (high inhibitory capacity) for L-, E- or P-selectin in a context of acidic or polar lipids (but not positively charged lipids). Where the saccharide is the non-sulfated sLe$^x$ analog, an acidic neighboring lipid is required for full inhibitory activity, which is selective for L- and P-selectin. Sulfate lipids support sLe$^x$ binding better than carboxylate lipids, even at a relative proportion of 50%. As in the preceding example, the presence of acid lipids turn ineffective neutral disaccharides like lactose and maltose into effective inhibitors. This effect occurred only for L- and P-selectin, since none of the neutral disaccharide compositions inhibited E-selectin binding. The contributory effect of acid groups to the binding of L- and P-selectin is consistent with the working hypothesis that the lipid acid groups fulfill a selectin binding requirement equivalent to what is provided by sulfotyrosine or its equivalent in the biological ligands.

This mixed construction approach combined with a simple plate-binding assay provides a rapid method for identifying carbohydrate-acid group combinations that are capable of selectively inhibiting the binding of different selectin-ligand pairs.

Example 4
Cell activity Assays Confirm Biological Efficacy of Glycoliposomes

Glycoliposomes containing 5% sulfo Le$^x$ analog and 95% hydroxyl-terminated lipid were tested in a flow adhesion assay (Alon et al., Nature 374:539, 1995). Briefly, P-selectin chimera is immobilized in a flow chamber and the affinity of HL-60 cells for this substrate is manifest for their ability to roll slowly along on the surface. The interaction is specific for the PSGL-1 mucin domain on the HL-60 cells and the inhibitor's ability to block cell adhesion under physiological flow rather than under static conditions. At a glycolipid concentration of 1 TM, this glycoliposome formulation was able to completely inhibit HL-60 cell rolling on P-selectin surfaces. The control liposome (without the carbohydrate) had no effect.

The same liposome formulation was tested in the Stamper-Woodruff lymphocyte homing assay (Stamper et al., J. Exp. Med. 144:828, 1976). This assay measures ability of lymphocytes to home into lymph nodes through high endothelial venules (HEV), a process known to be mediated by L-selectin. Thoracic duct lymphocytes (TDC) were counted on fixed sections of HEV in the presence of the liposomes. The 5% glycoliposome completely inhibited the TDC from binding to HEV at a concentration of 1 TM. The control liposome had no effect.

Example 5
Alternative Saccharide Components

Further refinement of the carbohydrate component of polymerized liposomes is conducted along several fronts.

Figures 7, 8:
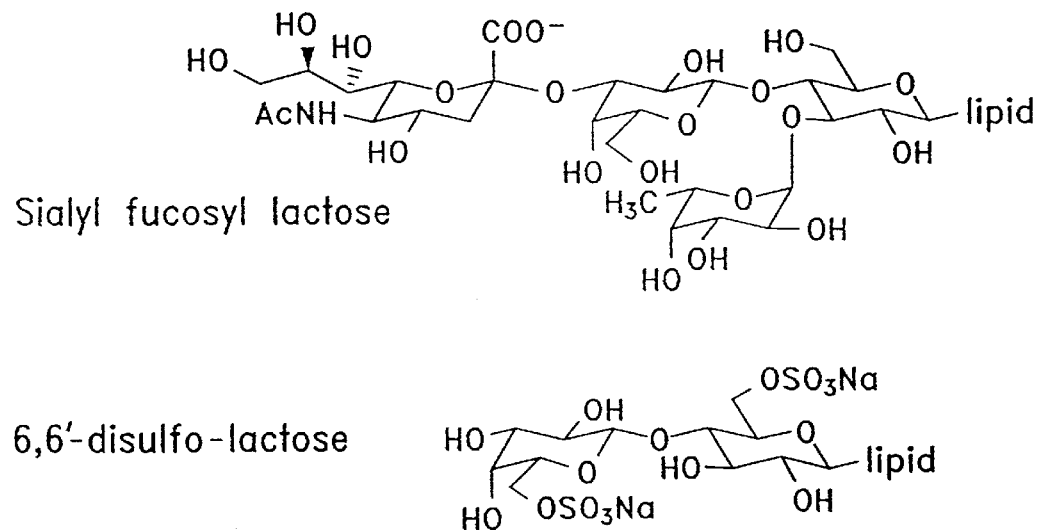
FIGS. 7 and 8 are drawings of additional exemplary carbohydrate determinants for inclusion in polymerized glycoliposomes.

In one experimental series, the prototype oligosaccharides sLe$^x$ and sulfo Le$^x$ are dissected into various substituents and tested in independent compositions. FIG. 7 shows some monosaccharide and disaccharide lipid conjugates of interest. Other saccharides of interest are lactosamine, 3' sialyl lactosamine, and 3' sialyl lactose. The identification of active subcomponent saccharides has two purposes. One is to further elucidate the binding requirements for each selectin, which can then be used to develop inexpensive analog structures with enhanced binding or selectin specificity. Another is to identify mono- and disaccharides that can be used in a mixed saccharide liposome, as explained below.

In another experimental series, other oligosaccharides believed to have equal or better activity than the prototypes as monomers are tested in liposome compositions to determine if the activity can be enhanced further. Conjugates of interest are shown in FIG. 8. Other conjugates of interest are various sLe$^x$ analongs and other structures listed elsewhere in the disclosure.

The conjugates are formed similarly to those in the previous examples: by formation of peracetylated beta-NAc-allyl glycoside, combined with cystamine hydrochloride under U.V. light, and then coupled directly with the activated acid of PDA.

Mixed saccharide liposomes have different saccharides conjugated to different lipids in the composition. It is proposed that the different saccharides can work in concert to supply the carbohydrate requirement for selectin binding, when presented in the context of other lipids satisfying the anionic binding requirement in a polymerized lipid sheet. Of particular interest is a combination of sialic acid and fucose, since these are believed to be the residues in sLe$^x$ responsible for selectin binding.

The sialic acid conjugate is prepared according to the standard method outlined in Spevak et al. J. Amer. Chem.

Soc. (1993) 115, 1146. The fucose conjugate is prepared as follows. First, the perbenzoylated, glycosylchloride of fucose is C-allylated by trimethylallylsilane and trimethylsilyltriflate (Hosomi et al. Tetrahedron Lett. 2383, 1984 to give the C-glycoside. This compound is deprotected by sodium/ammonia. The perbenzoylated C-glycoside of fucose is dissolved in t-butanol and added to refluxing, anhydrous ammonia, protected from moisture. Solid sodium metal is then added until the blue color persists for at least 20 min. The reaction is then quenched with ammonium chloride and the ammonia is allowed to evaporate. The solid residue is dissolved in water, brought to about pH 2 with conc. HCl and extracted with ethyl acetate several times. The combined organic solutions are dried with magnesium sulfate and filtered. After evaporation the C-glycoside product is purified by flash chromatography. The C-glycoside is dissolved with cystamine-hydrochloride (3 eq.) in degassed water to give a 1 molar sugar solution. The solution is kept under a constant blanket of nitrogen and irradiated with UV light (254 nm). After 12 hours the solution is neutralized with solid sodium bicarbonate, concentrated and flash chromatographed yielding the amine. This is dissolved in a minimal amount of methanol, added to this solution of NHS-PDA (1.2 eq.) and stirred for 12 hrs. The reaction is diluted with chloroform, washed with saturated, aqueous sodium bicarbonate, then dried with magnesium sulfate and filtered. After evaporation, the crude glycolipid residue is purified by flash chromatography.

Sialic acid conjugate and fucose conjugate are mixed at a ratio of 1:1 and then combined with PDA at 5 to 10% glycoconjugate as molar percent of total lipid. Vesicle formation and lipid polymerization proceed as normal to form a mixed glycoliposome with a surface structure shown in FIG. 9.

The polymerized lipid compositions described in this example are tested according to the assay described in Example 3.

Example 6
Therapeutic Testing in Animal Models

Polymerized liposome compositions having good inhibition activity in selectin binding assays are tested further for their efficacy in disease models. All trials are conduced in accordance and with the approval of the appropriate Animal Use Committee.

Myocardial ischemia and reperfusion injury are modeled according to protocols similar to those of Weyrich et al. (J. Clin. Invest. 91:2620, 1993), Murohara et al. (Cardiovascular Res. 30:965, 1995), and Ma et al. (Circulation 88:649, 1993). Briefly, adult mammals of a higher species (typically canine, feline, or ovine) are anesthetized, and a midstemal thoracotomy is performed. A silk ligature is tied around the left anterior descending coronary artery 8–10 mm from the origin. EKG and MABP are continuously monitored. The animals are allowed to stabilize, and then myocardial ischemia (MI) is induced by tightening the ligature to complete occlusion. The test therapeutic agent is given intravenously as a bolus 80 min later. At the 90 min time point, the ligature is untied and the myocardium is allowed to reperfuse for 270 min.

The ligature is retightened, and the aria at risk is identified by injecting Evans blue. After excision, irreversibly injured parts of the heart are identified by dissection and staining using 0.1% nitroblue tetrazolium, and calculated as a percentage of mass of the organ. The proportional area effected is reduced upon successful treatment. Myeloperoxidase activity in the ischemic myocardium as determined according to Mullane et al. (J. Pharmacol. Meth. 14:157, 1985) is preferably also reduced. The ischemic-reperfused coronary endothelium can also be measured for adherence of isolated autologous PMN, and is preferably reduced in the treated animals. The animals are tested in three groups: MI induced and inhibitor treated; MI induced and control treated; and sham MI (operated but without vessel occlusion).

Treated animals in the cited studies responded to 400 Tg/kg of sLe$^x$ presented as a phospholipid liposome, or 1 mg/kg of the anti-L-selectin monoclonal antibody DREG-200. In the present experiment, polymerized liposomes are tested in a range of about 10–400 Tg of carbohydrate equivalent per kg body weight. An equal number of polymerized liposomes made of 100% neutral lipids is given at an equal dose (on a per-liposome basis) as vehicle control. To the extent that necrosis induced by other types of acute cardiac inflammatory events, such as myocarditis, restenosis and deep vein thrombosis, are mediated by similar mechanisms, the effective doses established in the cardiac reperfusion model may also be considered for these conditions.

Lung reperfusion injury is modeled according to protocols similar to those of Steinberg et al. (J. Heart Lung Transplant 13:306, 1994) and Kapelanski et al. (J. Heart Lung Transplant 12:294, 1993). Briefly, general anesthesia is induced, and the left lung is exposed by excision of adjacent ribs, intercostal muscles and neurovasculature. After a 30 min recovery period, animals are selected for continuation that have an arterial oxygen tension above 200 mm Hg and a carbondioxide tension below 45 mm Hg. After systemic heparinization, ischemia of the left lung is initiated by occlusion of the left main pulmonary artery. The period of ischemia is about 3 h, whereupon the lung is ventilated and permitted to reperfuse. Ten minutes before reperfusion, animals receive a bolus intravenous infusion of the test therapeutic compound. Ten minutes after the onset of reperfusion, the right pulmonary artery is ligated, and the tip of an endotracheal tube is advanced beyond the orifice of the trachial bronchus, and the right main bronchus is clamped at end expiration. Physiologic parameters are recorded for 6 h. Animals are compared on the basis of survival data, plus several of the following: gravimetric lung water, partial pressures of oxygen and carbon dioxide, inert gas shunt, pulmonary vascular resistance, and circulating WBC, neutrophil and lymphocyte count. Sham animals are operated but the pulmonary artery is not ligated—both lungs are ventilated during the 3 h period, and then worked up as in the test animals.

In the first study cited above, ischemic animals responded to 1 mg/kg of the monoclonal antibody EL-246, specific for L- and E-selectin. In the present experiment, polymerized liposomes are tested in a range of about 10–400 Tg of carbohydrate equivalent per kg body weight. An equal number of polymerized liposomes made of 100% neutral lipids is given at an equal dose (on a per-liposome basis) as vehicle control.

Pulmonary vascular injury induced by hemorrhagic shock is modeled according to protocols similar to those of Kushimoto et al. (Thrombosis Res. 82:97, 1996). Briefly, adult rats are anesthetized with pentobarbital, the right carotid artery is cannulated for monitoring blood pressure, and the left femoral artery is cannulated for sampling blood and administering fluids. Phlebotomy is induced by gradual withdrawal of 25 mL blood/kg over 15 min using a syringe pump. The mean arterial pressure is maintained between ~30–40 mm Hg for 30 min, and then the rats are resuscitated with 75 mL/kg lactated Ringer's solution, infused over 30 min. Physiological body temperature was maintained during this procedure using a heat lamp. Sham animals are cannulated in the same fashion, but no blood is removed. Pulmonary accumulation of leukocytes, measured as myeloperoxidase activity, and pulmonary vascular permeability to bovine serum albumin (BSA) peaks at 6 h. The hemorrhagic shock is reversible, because animals surviving the first 6 h and allowed to recover survive for at least another 5 days.

The therapeutic compound is tested by administering boluses of test compound through the femoral artery cannula at regular intervals through the critical period (0, 2, and 4 h following fluid resuscitation). $^{125}$I-BSA is injected 30 min prior to sacrifice at the 6 h point. A midline laparotomy is performed, blood is withdrawn from the abdominal aorta, and the pulmonary vasculature is perfused with saline via right ventricular puncture. Pulmonary vascular permeability is calculated as a ratio cpm in lung versus plasma, and is an indication of pulmonary vascular damage. Lung samples are homogenized and assayed for myeloperoxidase activity according to Warren et al. (J. Clin. Invest. 84:1873, 1989), as an indication of the number of neutrophils in the lung. Reduction of myeloperoxidase activity and/or permeability by the test composition compared with vehicle control is an indication of efficacy.

In the cited study, hemorrhagic animals responded to 1 mg/kg of the monoclonal antibody PB 1.3. In the present experiment, polymerized liposomes are tested in a range of about 10–400 Tg of carbohydrate equivalent per kg body weight per administration.

Tumor metastasis is modeled according to protocols similar to those described in PCT application WO 96/34609. This model is based on the highly metastatic BL6 clone of the B16 melanoma cell line (Dr. Jean Starkey, Montana Stane U., Bozeman Mont.), or a similar line established and cloned by standard techniques from an excised melanoma or carcinoma. A suspension of metastatic cells is suspended and incubated for 5–10 min at 37° C. with the therapeutic test compound at various concentrations, or a vehicle control. Following incubation, about 2–5×10$^4$ cells in a volume of 200 TL are injected into the tail vein of 8 week old syngeneic mice. After about 3 weeks, the animals are sacrificed. Lung and liver are excised and fixed in 10% formaldehyde, and tumor cell colonies are counted under a dissecting microscope. Colonies with a diameter >1 mm are counted separately from smaller colonies. A positive result is indicated by a substantial reduction in the total number of colonies or in the proportion of larger colonies. Polymerized liposome preparations are tested in a range of 5 nM-10 TM final concentration of carbohydrate equivalent in the cell incubation mixture.

Allergic asthma is modeled according to protocols similar to those described in PCT application WO 96/35418. Briefly, adult sheep are selected on the basis of having an established early and late bronchial response to inhaled *Ascaris suum* antigen. Animals are restrained, and the nasal passages are topically anesthetized with lidocane. The animals are intubated with a cuffed endotracheal tube through the opposite nostril with a flexible fiber optic bronchoscope as guide. Pleural pressure is estimated with an esophageal balloon catheter. Lateral pressure is measured with a sidehole catheter (i.d. 2.5 mm) advanced through and positioned distal to the tip of the endotracheal tube. The tracheal and pleural pressure catheters are connected to a differential pressure transducer for measuring transpulmonary pressure. Airflow is measured by connecting the proximal end of the endotracheal tube to a pneumotachograph. Pulmonary flow resistance is calculated as the change in transpulmonary pressure divided by the change in flow at mid-tidal volume, averaged over 5 breaths. Thoracic gas volume is measured in a constant-volume body plethysmograph to obtain specific lung resistance ($SR_L$).

Aerosols of test therapeutic suspensions are generated using a nebulizer that provides a median aerodynamic diameter of ~3 Tm. The nebulizer is connected to a dosimeter system, consisting of a solenoid valve and a source of compressed air. The solenoid valve is activated for 1 sec at the beginning of the inspiratory cycle of the respirator. Aerosols are delivered at a tidal volume of 500 mL at a rate of 20 breaths per minute. The test therapeutic compound is administered via nebulizer. To assess bronchial responsiveness, cumulative concentration response curves are determined by measuring $SR_L$ immediately after inhalation of buffer, and after each consecutive administration of 10 breaths of increasing concentrations of carbachol, in the range of ~0.25% to ~4% (wt/vol). The test is discontinued when $SR_L$ exceeds 400% of initial value or the maximal dose is reached. Bronchial responsiveness is assessed by determining the point at which $SR_L$ reached 400%. Polymerized liposome preparations are tested in a range of 5 nM-10 TM final concentration of carbohydrate equivalent in the aerosol solution.

Arthritis is modeled according to the collagen type-II induced arthritis model of Zeidler et al. (Autoimmunity 21:245, 1995). Briefly, groups of age-matched DBA/1 mice are immunized intradermally with 100 Tg collagen type II from bovine cartilage, emulsified in complete Freund's adjuvant, followed 18 days later with 50 Tg in incomplete Freund's adjuvant. Test therapeutic compositions are administered weekly from about week 4 to about week 8 following the first collagen injection. The disease is assessed daily by visual signs of erythema, and of swelling of one or more joints. Immunological signs of autoimmunity are monitored by standard immunoassays for serum antibody against collagen type II, collagen type I, and proteoglycans. Reduction in the titers of the autoantibodies, or a delay in the appearance of visual signs of arthritis, are indications of efficacy. Polymerized liposomes are tested in a range of about 10–400 Tg of carbohydrate equivalent per kg body weight. In the present experiment, polymerized liposomes are tested in a range of about 10–400 Tg of carbohydrate equivalent per kg body weight per administration, or an equal number of control liposomes.

Other established animal models are implemented in the testing of polymerized liposomes for the treatment of additional clinical conditions of interest.

What is claimed as the invention is:

1. A composition for inhibiting binding between a first cell having a P- or L-selectin and a second cell having a ligand for the selectin, comprising a sheet of lipids wherein a proportion of the lipids sufficient to stabilize the sheet are covalently crosslinked, a proportion of the lipids have an attached saccharide which meets the carbohydrate binding requirements of selectins, and a proportion of the lipids not having an attached saccharide have an acid group that is negetively charged at neutral pH which meets the anionic binding requirement of P- and L-selectin.

2. The composition of claim 1, wherein the saccharide is a sialylated fucooligosaccharide or analog thereof.

3. The composition of claim 1, wherein the saccharide is a sulfated fucoohgosaocharide.

4. The composition of claim 1 wherein the attached saccharide is a neutral saccharide.

5. The composition of claim 1, wherein the saccharide is selected from the group consisting of lactose and maltose.

6. The composition of claim 1 wherein the attached sacdiaride is a disaccharide.

7. The composition of claim 1 wherein a proportion of the lipids having an attached saccharide are covalently crosslinked to other lipids in the sheet.

8. The composition of claim 1 wherein a proportion of lipids having an attached saccharide are not covalenty crosslinked to other lipids in the sheet.

9. The composition of claim 1, wherein a proportion of the lipids in the lipid sheet have a first attached saccharide, and a separate proportion of the lipids in the lipid sheet have a second attached saccharide that is different from the first.

10. The composition of claim 1, wherein the first attached saccharide is fucose and the second attached saccharide is a sulfated or acidic monosaccharide.

11. The composition of claim 1, wherein the acid group is a carboxylic acid.

12. The composition of claim 1, wherein the acid group is a negatively charged sulfate or phosphate group.

13. The composition of claim 1, wherein the lipid sheet is part of the lipid bilayer of a liposome.

14. The composition of claim 1, wherein the lipids each contain a single aliphatic hydrocarbon.

15. The composition of claim 1, wherein the composition inhibits binding of the ligand to the selectin.

16. The composition of claim 1, wherein the composition has a 50% inhibition concentration ($IC_{50}$) that is $10^2$-fold lower than that of monomer $sLe^x$.

17. The composition of claim 1, wherein the composition has a 50% inhibition concentration ($IC_{50}$) that is $10^4$-fold lower than that of monomer $sLe^x$.

18. The composition of claim 1, wherein the composition has an $IC_{50}$ in a selectin-to-cell binding assay of less than 100 nM.

19. The composition of claim 1, wherein the selectin is P-selectin.

20. The composition of claim 1, wherein the selectin is L-selectin.

* * * * *